(12) United States Patent
Alizoti et al.

(10) Patent No.: US 10,328,229 B2
(45) Date of Patent: Jun. 25, 2019

(54) VENTILATOR CIRCUIT, ADAPTER FOR USE IN VENTILATOR CIRCUIT AND METHODS FOR THE USE THEREOF

(71) Applicant: TRUDELL MEDICAL INTERNATIONAL, London (CA)

(72) Inventors: Neritan Alizoti, London (CA); James Schmidt, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 834 days.

(21) Appl. No.: 14/854,776

(22) Filed: Sep. 15, 2015

(65) Prior Publication Data

US 2016/0101259 A1   Apr. 14, 2016

Related U.S. Application Data

(63) Continuation of application No. PCT/IB2014/000349, filed on Mar. 14, 2014.
(Continued)

(51) Int. Cl.
*A61M 16/14*   (2006.01)
*A61M 11/00*   (2006.01)
(Continued)

(52) U.S. Cl.
CPC ............ *A61M 16/14* (2013.01); *A61M 11/00* (2013.01); *A61M 15/00* (2013.01);
(Continued)

(58) Field of Classification Search
CPC .... A61M 16/00; A61M 16/20; A61M 16/201; A61M 16/206; A61M 16/207; A61M 16/208; A61M 16/209; A61M 16/0816; A61M 16/0833; A61M 16/0875; F16K 1/00; F16K 1/48; F16K 13/00;
(Continued)

(56) References Cited

U.S. PATENT DOCUMENTS

| 584,091 A | 6/1897 | Leidich |
| 1,996,900 A * | 4/1935 | Backner ............... F16L 37/248 |
| | | 137/613 |

(Continued)

FOREIGN PATENT DOCUMENTS

| EP | 1066850 B1 | 8/2006 |
| GB | 558607 | 1/1944 |

(Continued)

*Primary Examiner* — Michael J Tsai
(74) *Attorney, Agent, or Firm* — Brinks Gilson & Lione

(57) ABSTRACT

An adapter includes a housing having an inlet port defining a flow path and an outlet port. An interior wall has an inner surface defining an interior passageway communicating with the outlet port and an exterior surface defining an exterior passageway communicating with the inlet port. The interior wall defines a mouth communicating between the interior and the exterior passageways. The interior wall is positioned transverse to the flow path of the inlet port. A medicament delivery port opens into the mouth. A valve is moveable between a closed position, wherein the valve closes the medicament delivery port, and an open position, wherein the medicament delivery port is open. A ventilator circuit and method of delivering a medicament are also provided.

26 Claims, 31 Drawing Sheets

Related U.S. Application Data

(60) Provisional application No. 61/791,904, filed on Mar. 15, 2013.

(51) Int. Cl.
  *A61M 15/00* (2006.01)
  *A61M 16/20* (2006.01)
  *A61M 16/08* (2006.01)
  *A61M 11/06* (2006.01)
  *A61M 16/04* (2006.01)

(52) U.S. Cl.
  CPC ...... *A61M 15/009* (2013.01); *A61M 15/0025* (2014.02); *A61M 15/0065* (2013.01); *A61M 16/0833* (2014.02); *A61M 16/20* (2013.01); *A61M 11/005* (2013.01); *A61M 11/007* (2014.02); *A61M 11/06* (2013.01); *A61M 15/0085* (2013.01); *A61M 16/0463* (2013.01); *A61M 2202/0208* (2013.01); *A61M 2205/02* (2013.01)

(58) Field of Classification Search
  CPC ........ F16K 1/2085; F16K 1/2266; F16K 3/20; F16K 5/161; F16K 31/445; F16L 37/38; F16L 37/40; F16L 37/42
  See application file for complete search history.

(56) References Cited

U.S. PATENT DOCUMENTS

| | | | |
|---|---|---|---|
| 2,688,979 A | 9/1954 | Kendrick | |
| 2,710,623 A | 6/1955 | Kolos | |
| 2,777,716 A * | 1/1957 | Gray | F16L 37/0841 251/149.6 |
| 2,820,651 A * | 1/1958 | Phillips | F16L 27/087 128/204.18 |
| 2,822,819 A | 2/1958 | Geeraert | |
| 3,174,434 A | 3/1965 | Schieve | |
| 4,930,498 A | 6/1990 | Hayek | |
| 4,938,210 A | 7/1990 | Schene | |
| 4,951,661 A * | 8/1990 | Sladek | A61M 16/0808 128/202.27 |
| 5,164,740 A | 11/1992 | Ivri | |
| 5,241,954 A | 9/1993 | Glenn et al. | |
| 5,396,883 A | 3/1995 | Knupp et al. | |
| 5,443,452 A | 8/1995 | Hart et al. | |
| 5,461,695 A | 10/1995 | Knoch | |
| 5,586,550 A | 12/1996 | Ivri et al. | |
| 5,696,883 A | 12/1997 | Arima | |
| 5,758,637 A | 6/1998 | Ivri et al. | |
| 5,938,117 A | 8/1999 | Ivri | |
| 6,014,970 A | 1/2000 | Ivri et al. | |
| 6,014,972 A * | 1/2000 | Sladek | A61M 15/0065 128/203.12 |
| 6,085,740 A | 7/2000 | Ivri et al. | |
| 6,205,999 B1 | 3/2001 | Ivri et al. | |
| 6,367,470 B1 | 4/2002 | Denyer et al. | |
| 6,382,255 B2 | 5/2002 | McFarland | |
| 6,412,481 B1 | 7/2002 | Bienvenu | |
| 6,615,824 B2 | 9/2003 | Power | |
| 6,629,646 B1 | 10/2003 | Ivri | |
| 6,701,922 B2 | 3/2004 | Hindle et al. | |
| 6,725,858 B2 | 4/2004 | Loescher | |
| 6,948,591 B2 | 9/2005 | Scott et al. | |
| 6,968,840 B2 | 11/2005 | Smith et al. | |
| 7,100,600 B2 | 9/2006 | Loeffler et al. | |
| 7,201,167 B2 | 4/2007 | Fink et al. | |
| 7,267,121 B2 | 9/2007 | Ivri | |
| 7,290,541 B2 | 11/2007 | Ivri et al. | |
| 7,322,349 B2 | 1/2008 | Power | |
| 7,600,511 B2 | 10/2009 | Power et al. | |
| 7,669,595 B1 | 3/2010 | Mitchell | |
| 7,686,014 B2 | 3/2010 | Boehm et al. | |
| 7,971,588 B2 | 7/2011 | Fink et al. | |
| 8,746,241 B2 | 6/2014 | Cavendish | |
| 2002/0134374 A1 | 9/2002 | Loeffler et al. | |
| 2002/0134375 A1 | 9/2002 | Loeffler et al. | |
| 2002/0162554 A1 * | 11/2002 | Loescher | A61M 16/08 128/205.24 |
| 2003/0222238 A1 | 12/2003 | Getzewich et al. | |
| 2004/0069308 A1 * | 4/2004 | Bayron | A61M 16/0463 128/207.16 |
| 2004/0096402 A1 | 5/2004 | Hodges et al. | |
| 2005/0217666 A1 | 10/2005 | Fink et al. | |
| 2005/0229927 A1 | 10/2005 | Fink et al. | |
| 2007/0240709 A1 * | 10/2007 | Woolley | A61M 16/08 128/200.21 |
| 2008/0027372 A1 | 1/2008 | Baldwin | |
| 2008/0210242 A1 * | 9/2008 | Burk | A61M 16/06 128/206.21 |
| 2009/0025722 A1 | 1/2009 | Pieper et al. | |
| 2009/0173344 A1 * | 7/2009 | Short | A61M 16/0066 128/203.12 |
| 2010/0126502 A1 | 5/2010 | Fink et al. | |
| 2011/0011395 A1 | 1/2011 | Mazela | |
| 2011/0247616 A1 * | 10/2011 | Von Hollen | A61M 16/0816 128/203.12 |
| 2013/0126011 A1 * | 5/2013 | Abraham | F16K 13/00 137/315.01 |

FOREIGN PATENT DOCUMENTS

| | | |
|---|---|---|
| WO | WO 97/29799 A2 | 8/1997 |
| WO | WO 01/83011 A1 | 11/2001 |
| WO | WO 03/059413 A2 | 7/2003 |
| WO | WO 2007141201 A1 | 12/2007 |

* cited by examiner

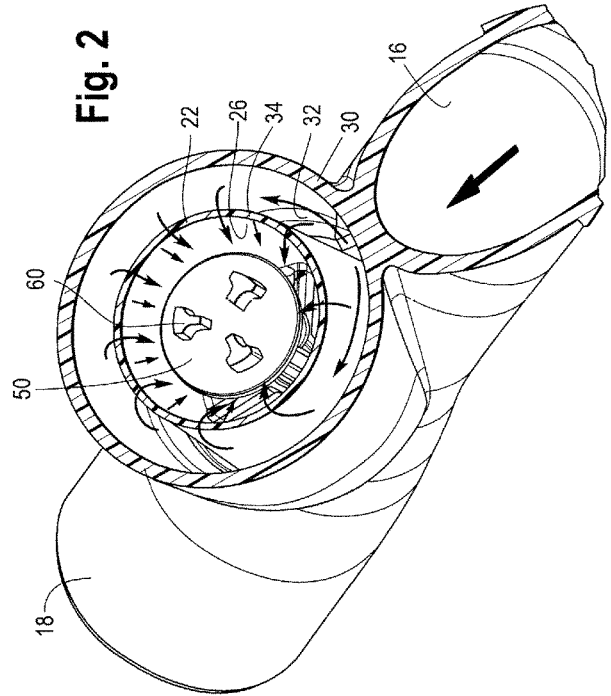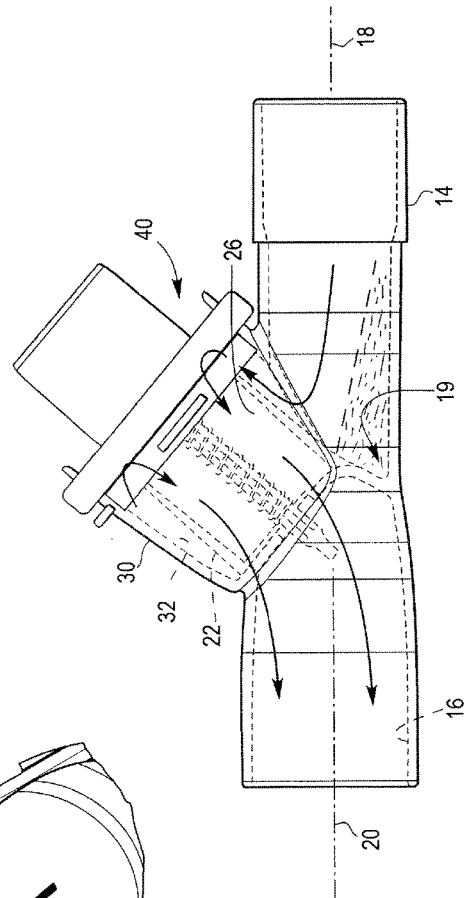

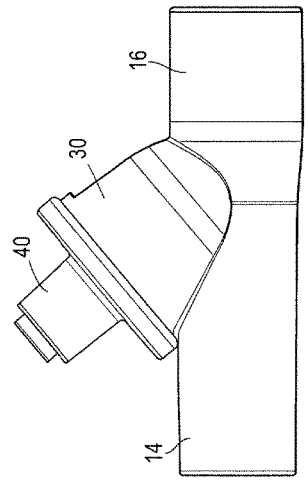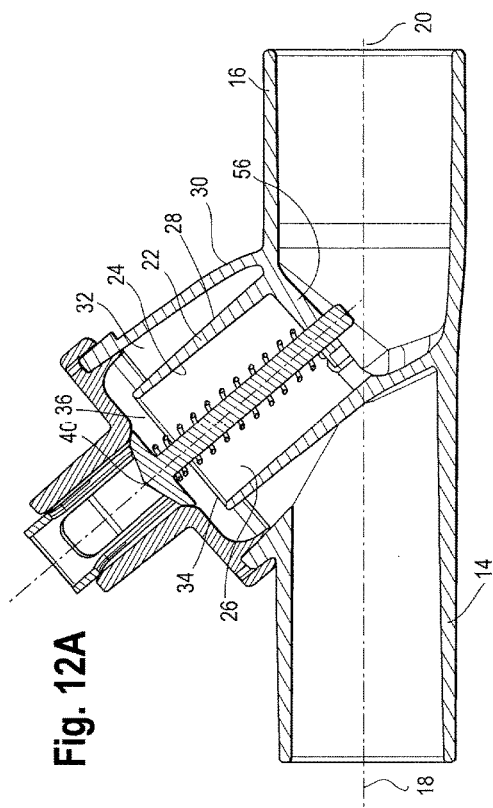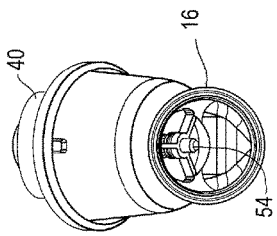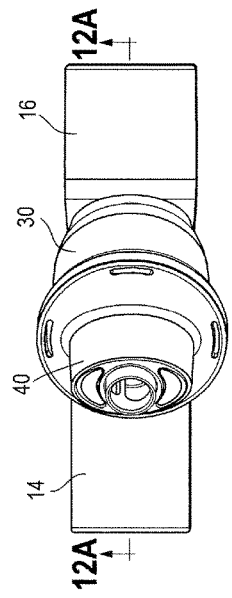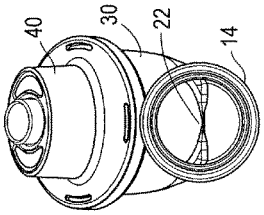

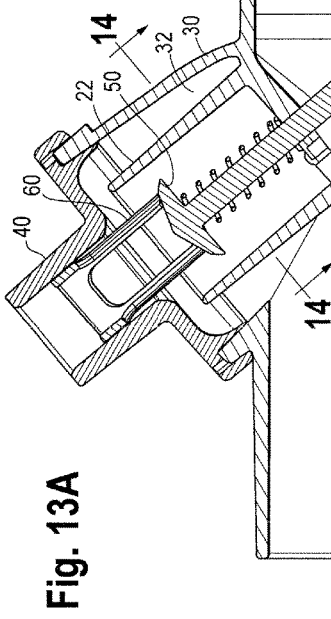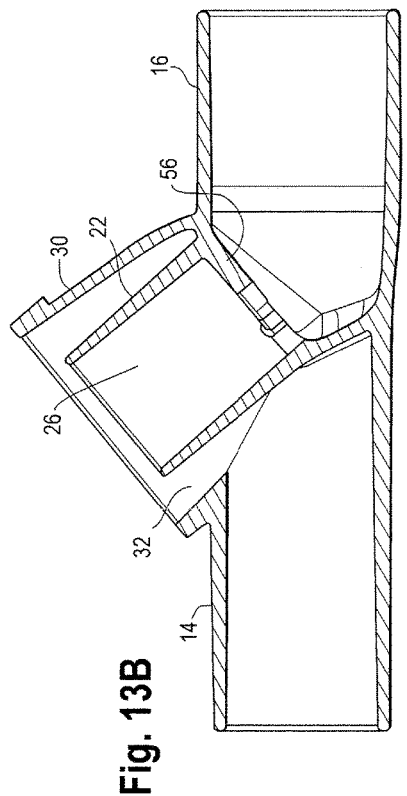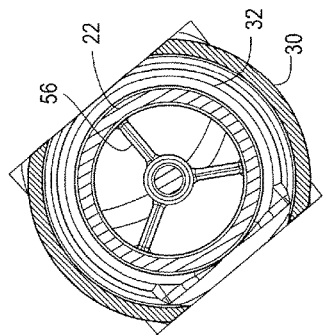

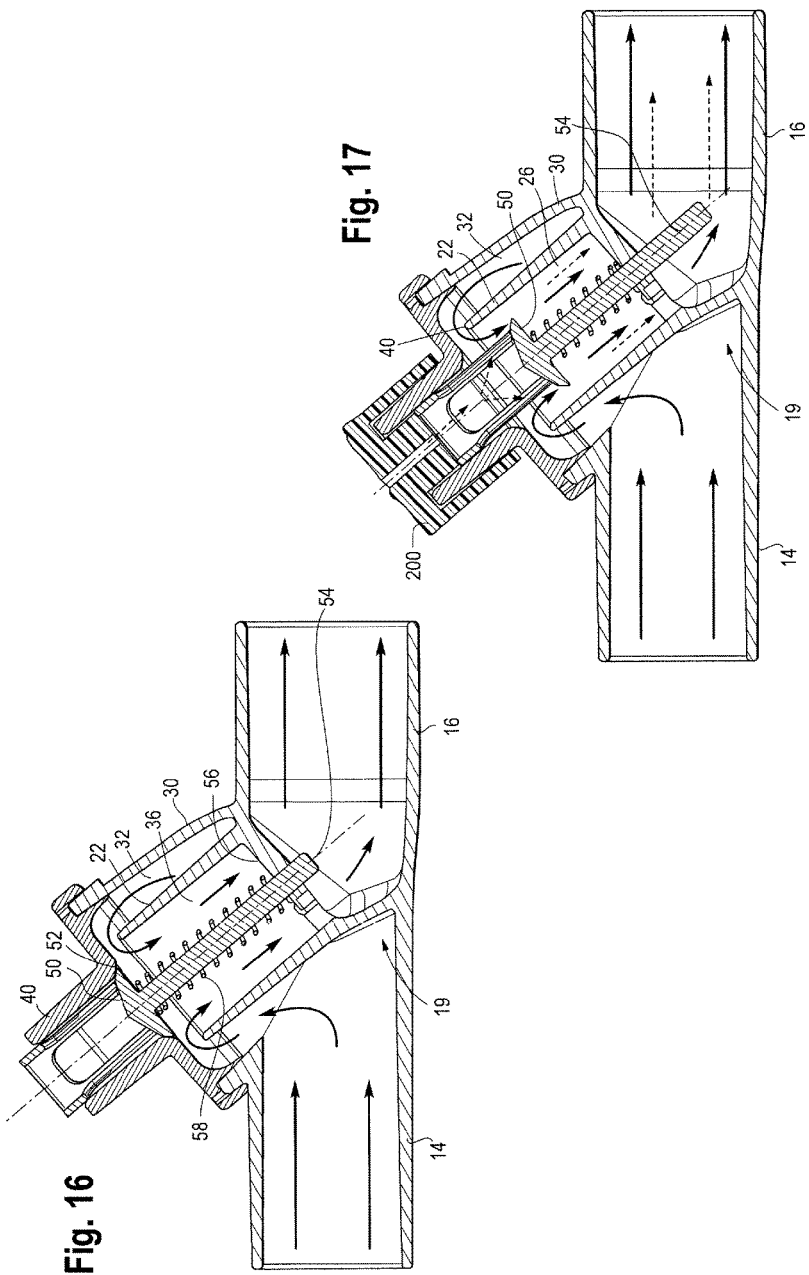

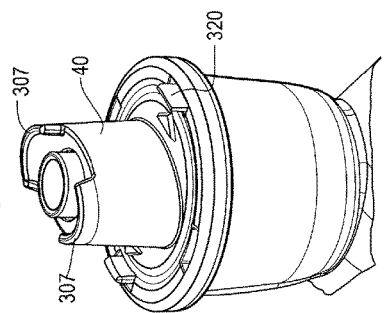
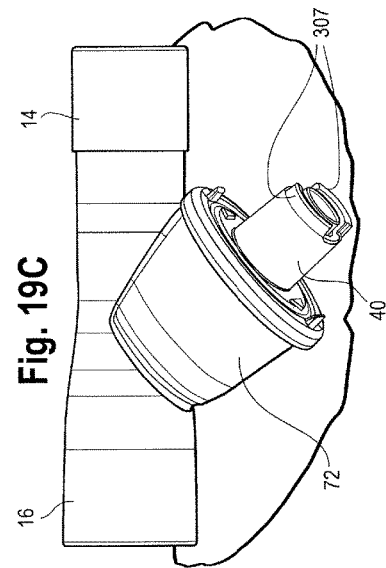
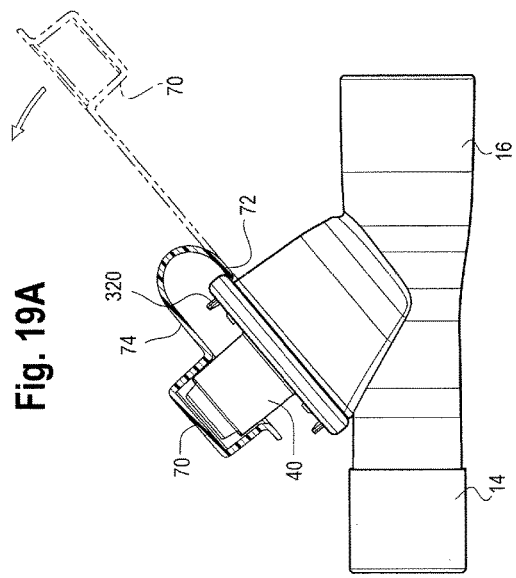

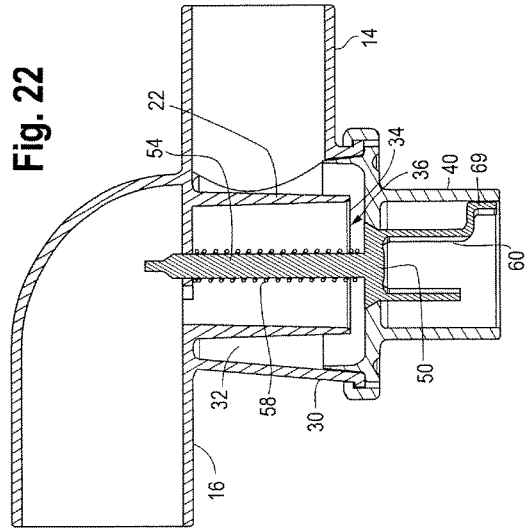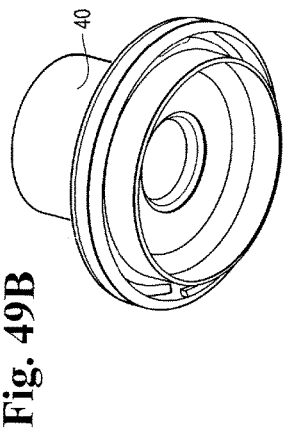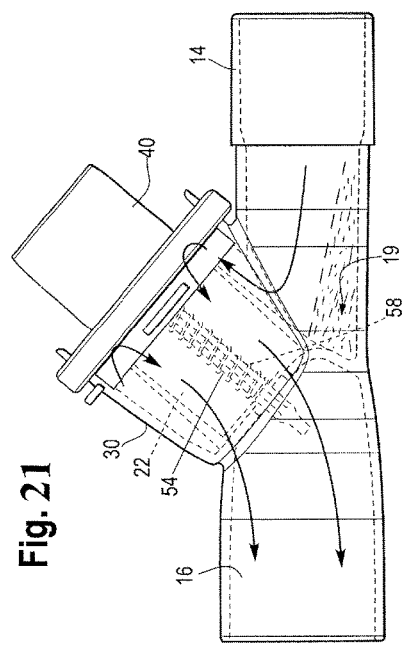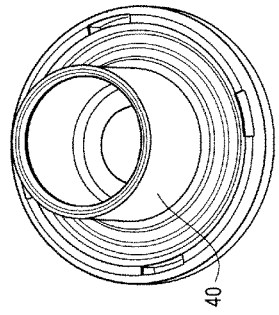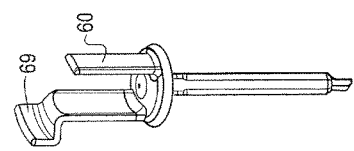

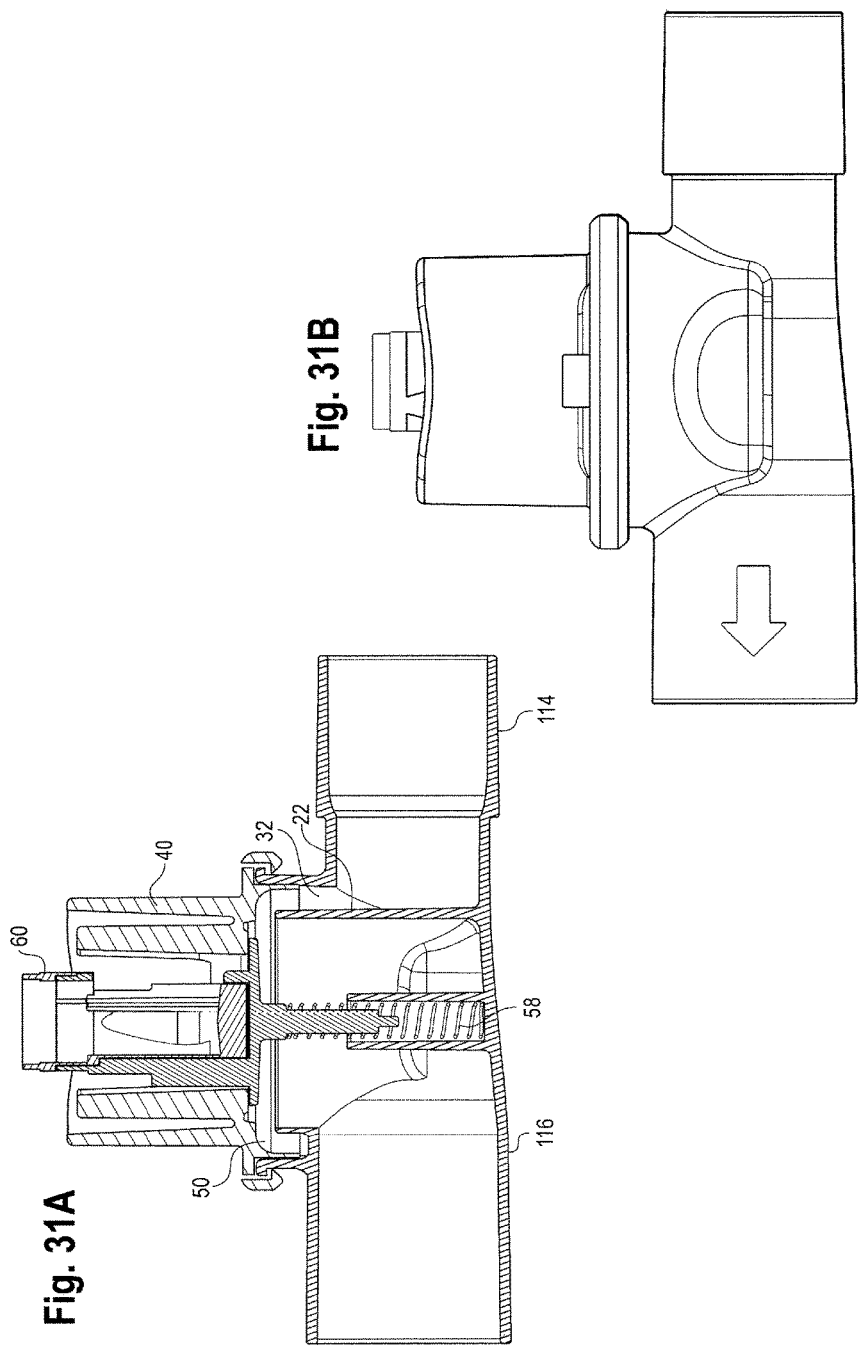

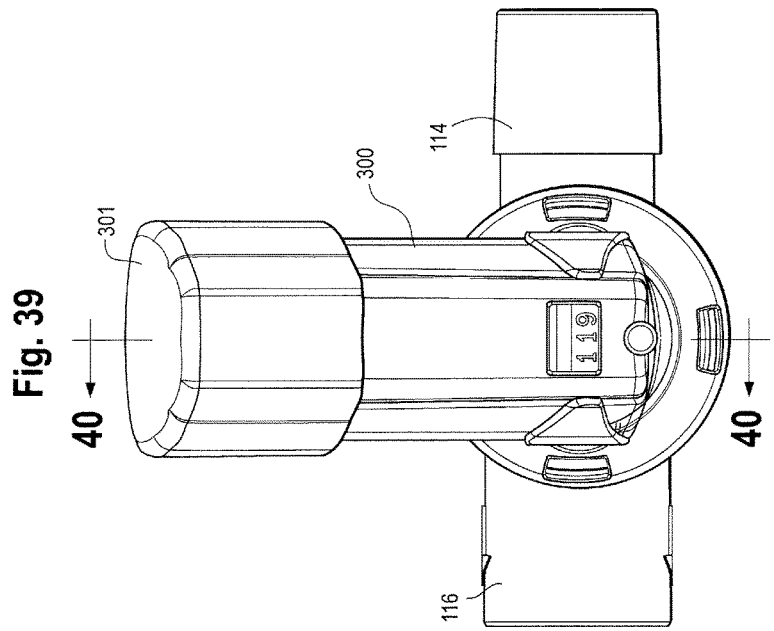
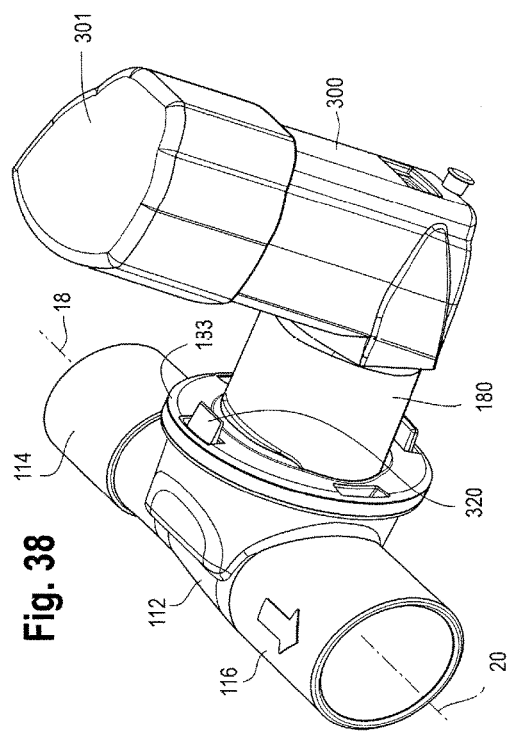

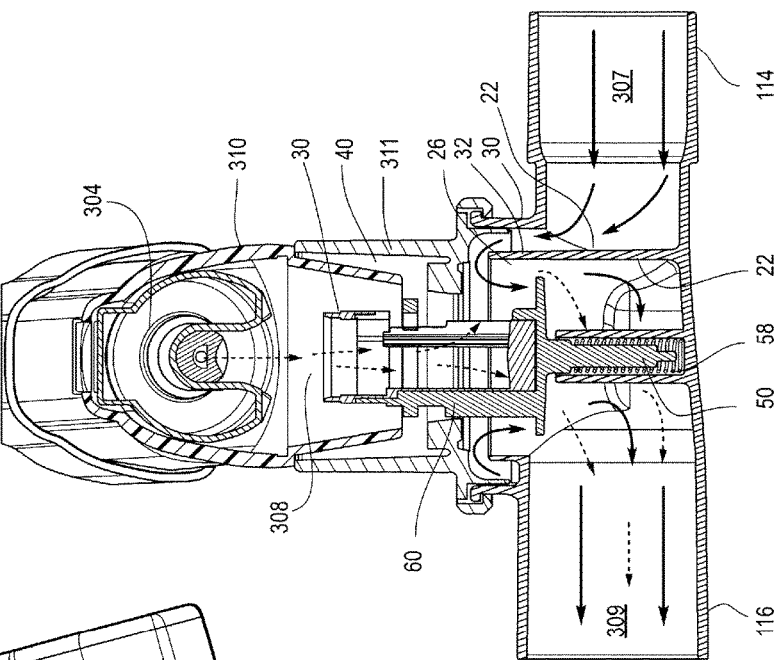
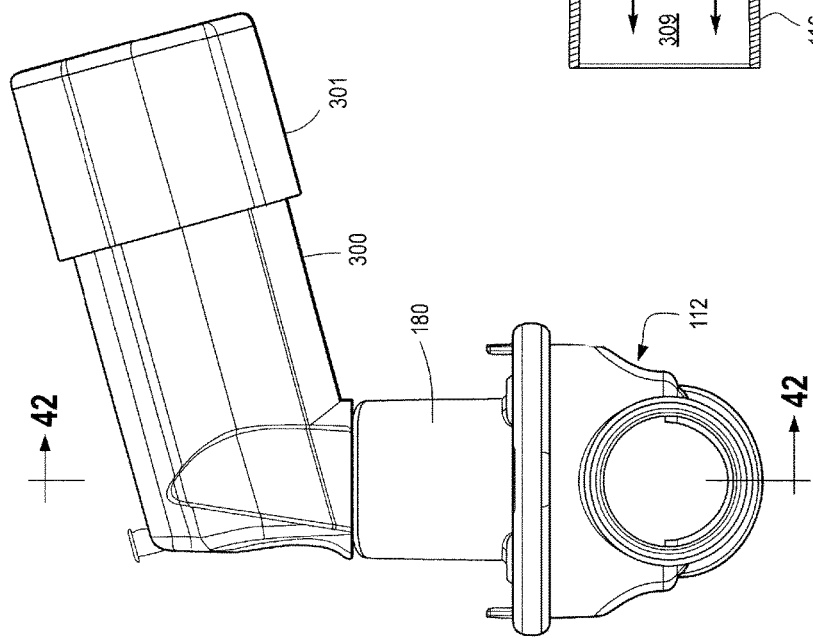

VENTILATOR CIRCUIT, ADAPTER FOR USE IN VENTILATOR CIRCUIT AND METHODS FOR THE USE THEREOF

This application is a continuation of International Application PCT/IB2014/000349, filed Mar. 14, 2014, which application claims the benefit of U.S. Provisional Application No. 61/791,904, filed Mar. 15, 2013, the entire disclosures of which are hereby incorporated herein by reference.

TECHNICAL FIELD

The present invention relates generally to an adapter for delivering a medicament in ventilator circuit, and to a ventilator circuit and methods for the use thereof.

BACKGROUND

It is well known to deliver aerosolized medicaments to a patient via various devices, including nebulizers and aerosol dispensing devices, such as pressurized Metered Dose Inhalers (PMDI's), in order to treat various conditions and diseases, including but not limited to various respiratory conditions and diseases such as asthma. Often, it is desirable and necessary to deliver such medicaments to a patient interfacing with a ventilator circuit. To provide such medicaments, an adapter may be positioned within the circuit to provide access for a medicament delivery device. Known adapters, however, are not suitable for interfacing with various medicament delivery devices Respimat Soft Mist Inhaler. In addition, such adapters typically are not self-sealable, but instead require a sealing cap to be re-placed after each use in order to seal the ventilator circuit from leaks or contamination In addition, while some known adapters may allow for the introduction of a medicament into a ventilator gas flow, the medicament may not be fully entrained or mixed, thereby reducing the amount of uniformity in the drug delivery to the patient.

SUMMARY

Briefly stated, in one aspect, one embodiment of an adapter includes a housing having an inlet port defining a flow path and a outlet port. An interior wall has an inner surface defining an interior passageway communicating with the outlet port and an exterior surface defining an exterior passageway communicating with the inlet port. The interior wall defines a mouth communicating between the interior and the exterior passageways. The interior wall is positioned transverse to the flow path of the inlet port. A medicament delivery port opens into the mouth. A valve is moveable between a closed position, wherein the valve closes the medicament delivery port, and an open position, wherein the medicament delivery port is open.

In another aspect, one embodiment of a ventilator circuit includes an oxygen supply communicating with the inlet port and an a user interface communicating with the outlet port. A medicament delivery device may be in communication with the medicament delivery port.

In another aspect, a method of delivering a medicament includes introducing a gas to an inlet port of an adapter along a flow path, circulating the gas around an exterior passageway defined by an exterior surface of an interior wall, wherein the interior wall is positioned transverse to the flow path of the inlet port, and passing the gas through a mouth of the interior wall into an interior passageway defined by an inner surface of the inner wall. The method further includes introducing a medicament through a medicament delivery port opening into the mouth and thereby entraining the medicament with the gas, and delivering the medicament to a user through an outlet port of the adapter communicating with the interior passageway.

The present embodiments of the invention, together with further objects and advantages, will be best understood by reference to the following detailed description taken in conjunction with the accompanying drawings.

BRIEF DESCRIPTION OF THE DRAWINGS

FIG. 2 is a top cross-sectional view taken along line 2-2 of FIG. 1.

FIG. 3 is a cross-sectional view of the adapter shown in FIG. 1 with the valve closed.

FIGS. 12A-E show a cross-sectional view, and side, top, front and rear views, of the adapter shown in FIG. 10 with the valve in a closed position.

FIGS. 13A and B show cross-sectional views of the adapter shown in FIG. 10 with the valve in an open position in FIG. 13A and without the valve in FIG. 13B.

FIG. 14 shows a cross-sectional view taken along line 14-14 in FIG. 13.

FIG. 16 shows a cross-sectional view of an adapter with a valve in a closed position.

FIG. 17 shows a cross-sectional view of an adapter with a valve in an open position.

FIGS. 19A-C show a side view, partial top view and isometric view of the adapter shown in FIG. 18.

FIG. 21 shows a cross-sectional view of an adapter with a valve in a closed position.

FIG. 22 shows a cross-sectional view of an alternative embodiment of an adapter.

FIGS. 31A and B show a cross-sectional view and a side view of an alternative embodiment of an adapter.

FIG. 38 shows an alternative embodiment of an adapter coupled to a pressurized metered dose inhaler.

FIG. 39 shows a side view of the embodiment shown in FIG. 38.

FIG. 41 shows an end view of the embodiment shown in FIG. 28.

FIG. 42 shows a cross-sectional view of the embodiment taken along line 42-42 of FIG. 41.

FIG. 48 shows a perspective view of one embodiment of an actuator.

FIGS. 49A and B show top and bottom perspective views of one embodiment of a port.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" ports may refer to any sequence of such members, and is not limited to the first and second ports of a particular configuration unless otherwise specified. It should be understood that the terms "input port" and "outlet port" refer to the function of the ports during an inhalation phase, and that the ports may serve the opposite function (removal or exit) during an exhalation phase. It should be understood that the term "communicates" refers to a fluid communication, and may be direct or indirect, for example through an intervening passageway.

Figure 5:
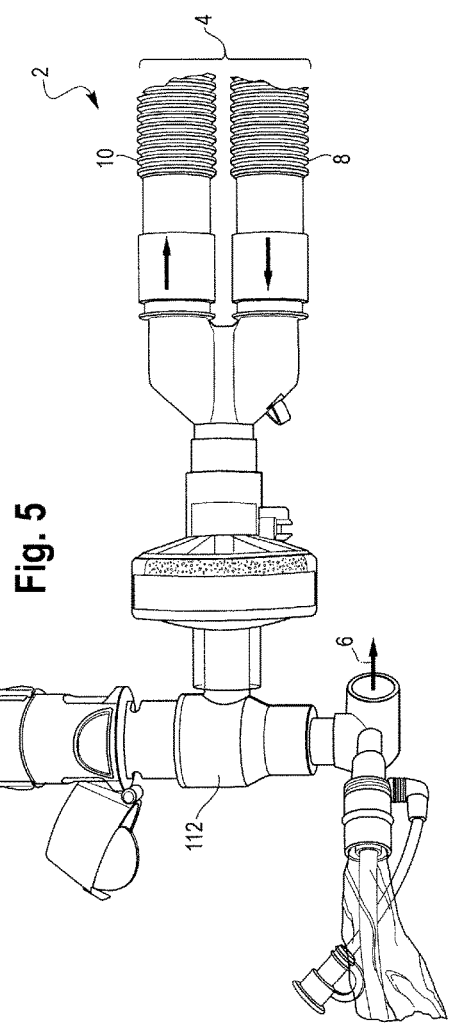
FIG. 5 is a view showing an adapter in a ventilator circuit.
Figure 7:
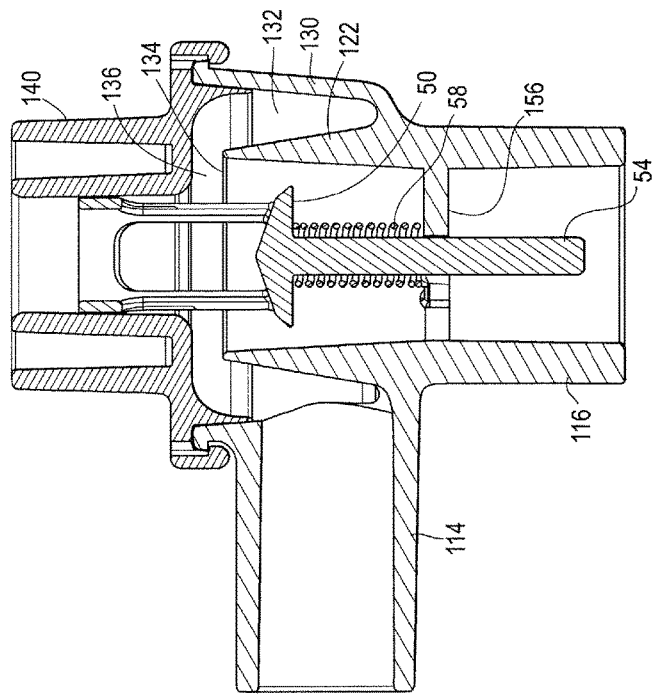
FIG. 7 is a cross-sectional view of one embodiment of an adapter with a valve in a open position.
Figure 6:
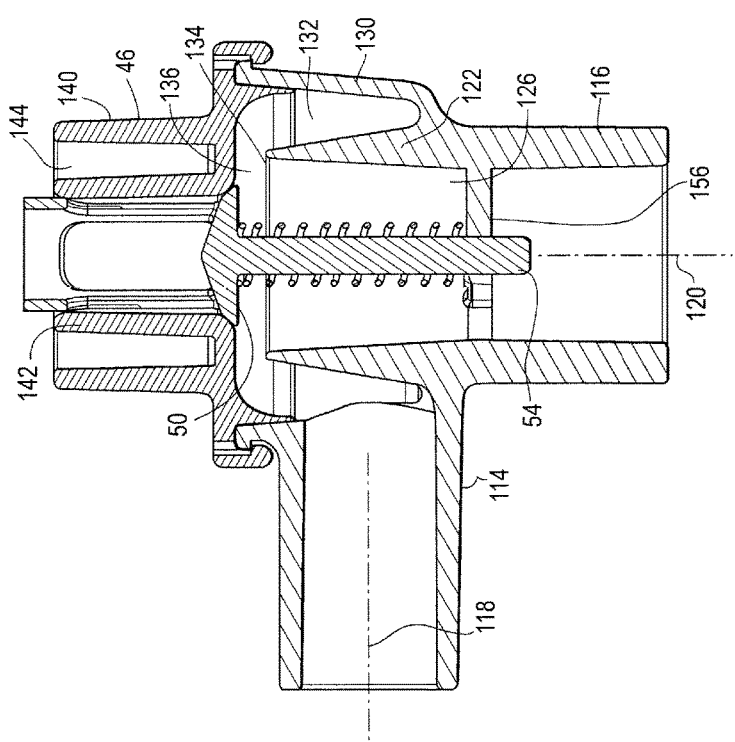
FIG. 6 is a cross-sectional view of one embodiment of an adapter with a valve in a closed position.
Figure 9:
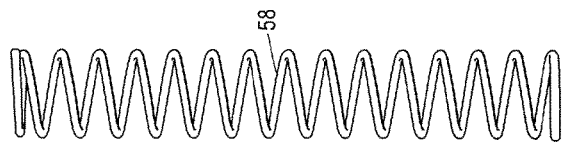
FIG. 9 shows a biasing spring for the valve.
Figure 8E:
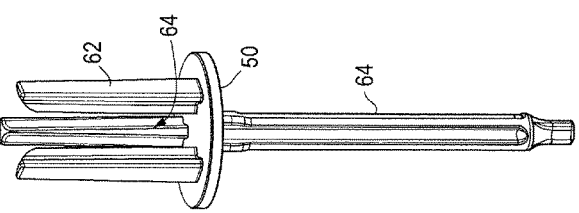
FIGS. 8A-E show different valve actuator embodiments.
Figure 8D:
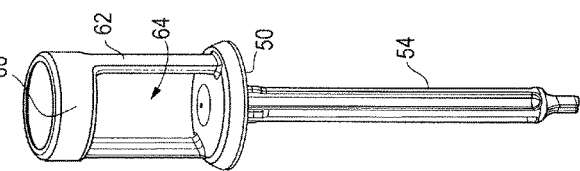
Figure 8C:
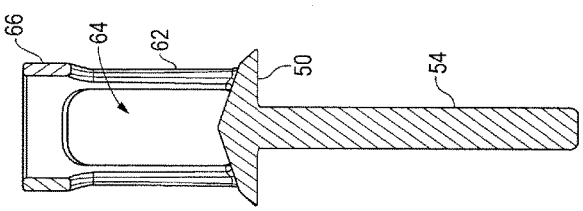
Figure 8B:
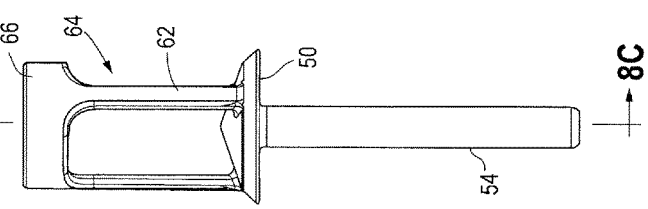
Figure 8A:
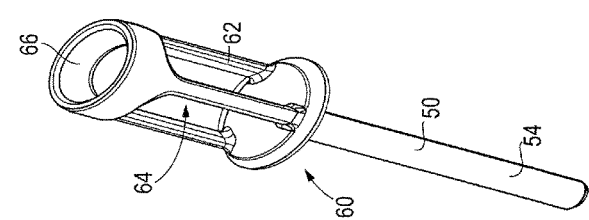
Figure 11:
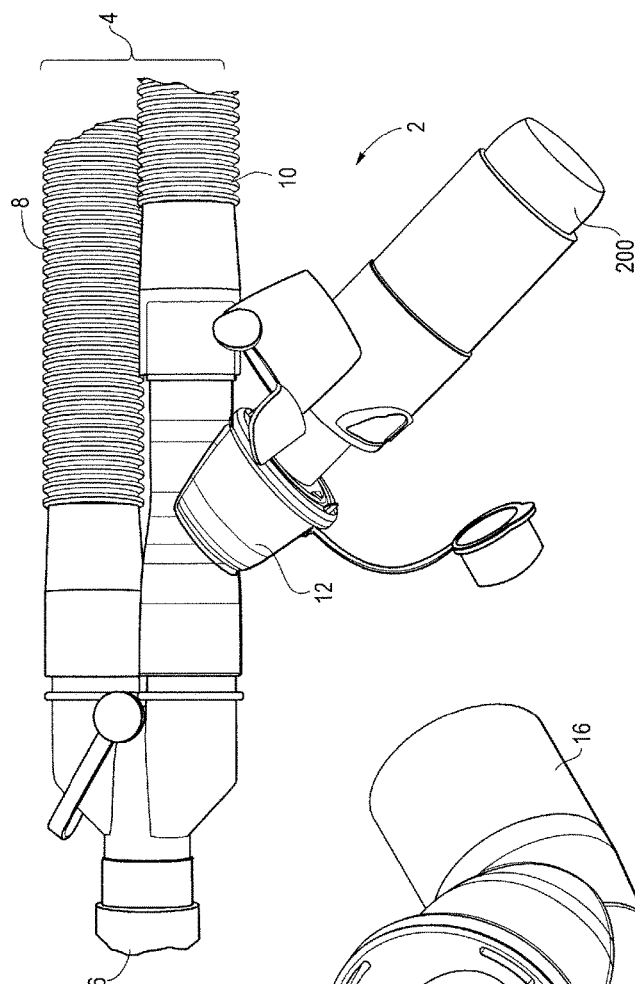
FIG. 11 shows the adapter of FIG. 10 in a ventilator circuit.
Figure 10:
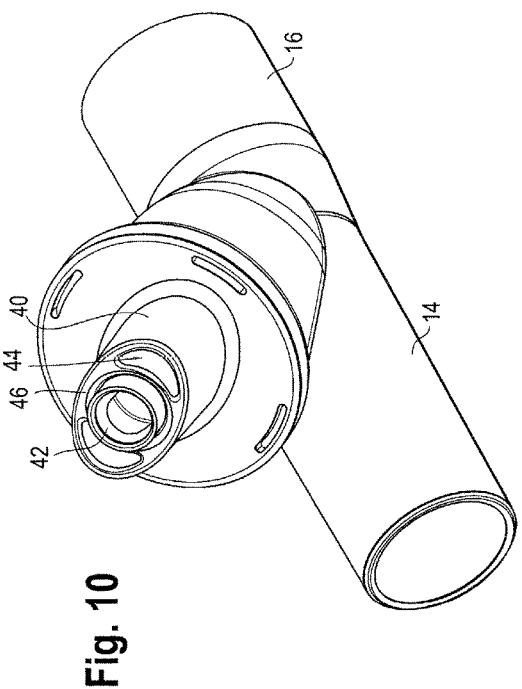
FIG. 10 shows a perspective view of another embodiment of an adapter.
Figure 15:
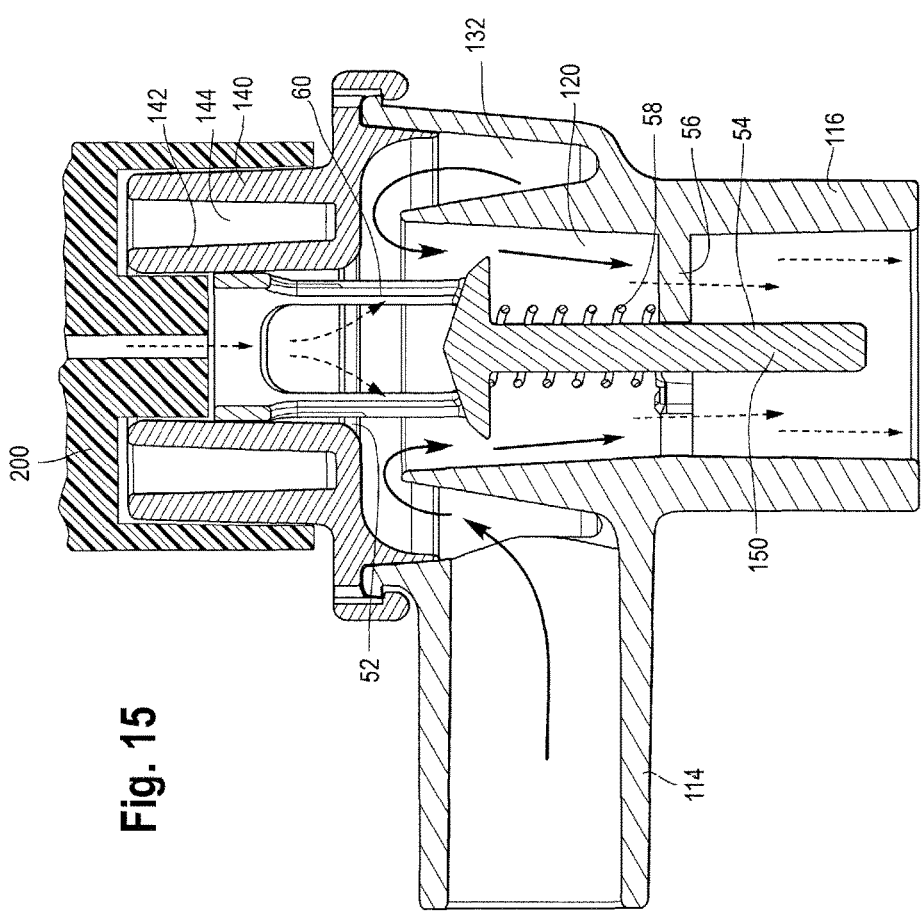
FIG. 15 shows a cross-sectional view of an adapter with a valve in an open position.

Referring to FIGS. 5 and 10, a ventilator circuit 2 is shown as including a ventilator 4 providing a gas supply, such as oxygen. Inlet and outlet lines 8, 10 may communicate with the ventilator 4. A user interface 6, such as a mask, tracheotomy tube, or mouthpiece is in communication with the gas supply.

Figure 1:
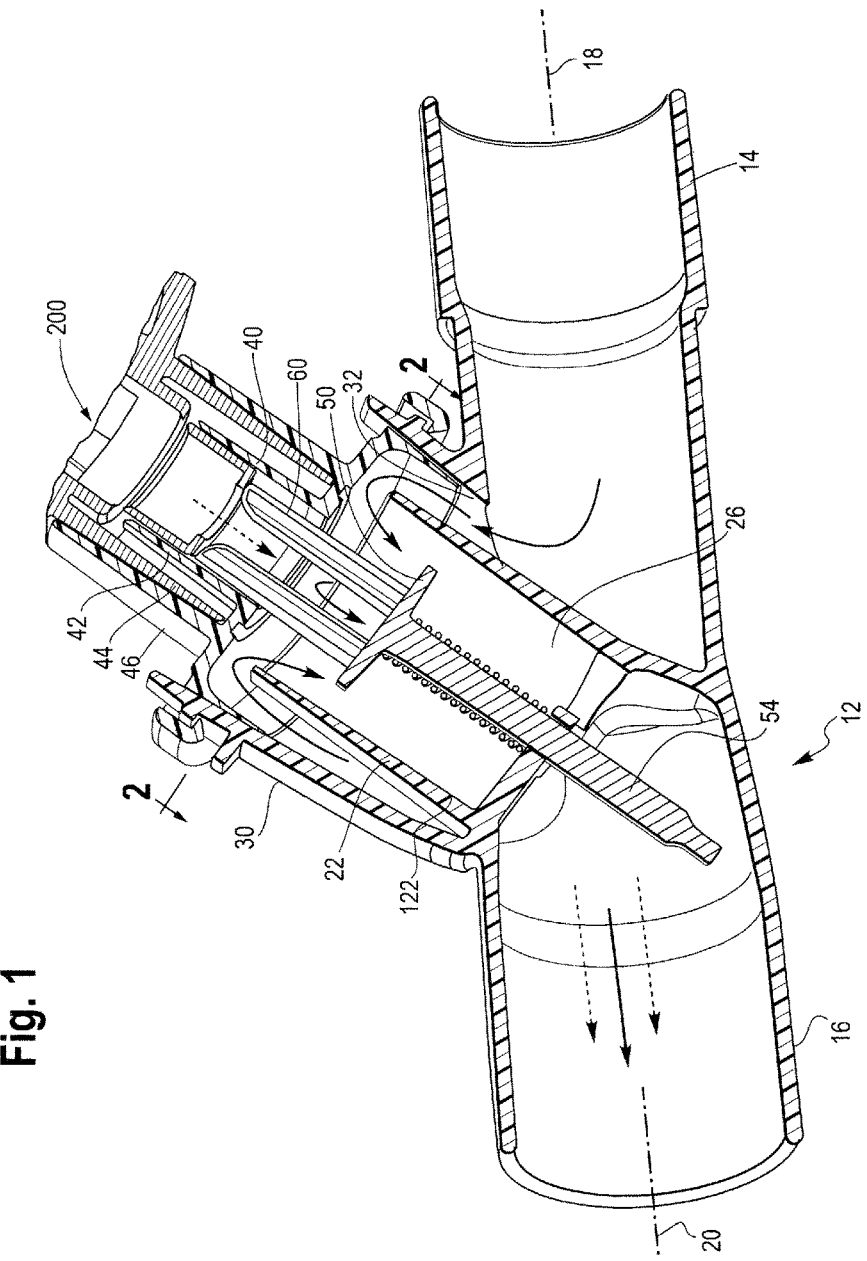
FIG. 1 is a cross-sectional view of an adapter with a medicament delivery device inserted therein.
Figure 4:
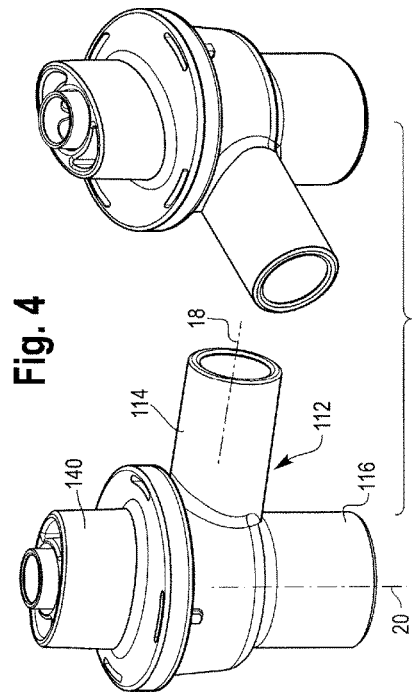
FIG. 4 is a perspective view of one embodiment of an adapter.

Referring to FIGS. 1-7, 10-26, 31-42, and 45-47 the ventilator circuit also includes an adapter 12, 112 inserted in the flow path between the ventilator and the user interface. The adapter 12, 112 includes a housing having an inlet port 14, 114 defining a flow path and communicating with the ventilator 4, and an outlet port 16, 116 communicating with the user interface 6. The inlet port 14, 114 defines a flow path 18 that may be parallel to the flow path 20 of the outlet port as shown in FIG. 1, or extending transversely thereto, for example in an orthogonal relationship as shown in FIG. 4.

Referring to FIGS. 1-7, 10-26, 33-35, 40, 42 and 45-47 the housing further includes an interior wall 22, 122 having an inner surface 24, 124 defining an interior passageway 26, 126 communicating with the outlet port and an exterior surface 28, 128 defining an exterior passageway 32, 132 communicating with the inlet port. An outer wall 30, 130 surrounds the inner wall and further defines the exterior passageway. The interior wall has a free end 34, 134 defining a mouth 36, 136 communicating between the interior and exterior passageways. The interior wall 22 is positioned transverse to at least a portion of the flow path 18 of the inlet port. The term "transverse" means lying or being across, for example the wall extends across the flow path of the inlet port, and is not limited to an orthogonal relationship. For example, the interior wall may extend orthogonal to the flow path as shown in FIG. 4, or may form an acute angle α (e.g. between about 40 and 60 degrees in various embodiments, and about 50 degrees in one embodiment) relative thereto as shown in FIG. 1. The wall may extend across the entirety of the cross-section of the flow path of the inlet port, as shown for example in FIGS. 4 and 12, or may extend across only a portion thereof.

Referring to FIGS. 1-7, 10-26, 33-42, and 45-47, the adapter housing further includes a medicament delivery port 40 opening into at least one of the exterior and interior passageways 26, 32, for example at the mouth 36, above the mouth, or below the mouth. The port 40, 140 may include a central channel defining the delivery opening formed by an annular wall 42, 142, and a surrounding peripheral channel 44, 144 formed by another wall 46, 146. A valve 50 is moveable between a closed position, wherein the valve is seated on a valve seat 52 and closes the opening of the delivery port as shown in FIGS. 3, 6, 12A-E, 16, 21, 23, 28, 33 and 46, and an open position wherein the medicament delivery port is open as shown in FIGS. 1, 2, 13, 15, 17, 24-26, 29, 30, 34, 35, 37, 42 and 45. The valve includes a stem 54 that moves axially relative to a baffle or guide 56, 156 formed between the interior passageway 26, 126 and the outlet port 16, 116. A spring 58 is disposed around the valve stem 54 and biases the valve to a closed position against the seat 52 on the medicament delivery port. The port 40 may be configured as a cap member that closes the stop of the exterior passageway as shown in FIGS. 20 and 49A-50B.

Referring to FIGS. 1-7, 10-26 and 33-37, the exterior passageway 32, 132 extends around an entire periphery of the internal wall 22, 122, which means in one embodiment, the exterior passageway completely encircles the wall, formed as an annular wall, providing a 360 degree passageway around the wall.

An actuator 60 is attached to the end of the valve 50 as shown for example in FIGS. 8A-E and 48. In various embodiments, the actuator includes at least one side opening 64 formed therein. The actuator may be configured with a plurality of arms 62 (shown as two or three, although it could be more) defining a plurality of side openings 64 therebetween. A collar 66 may join the ends of the arms. The collar 66, or free ends 68, 69 of the arms, engage an end of the medicament delivery device 200.

Figure 18:
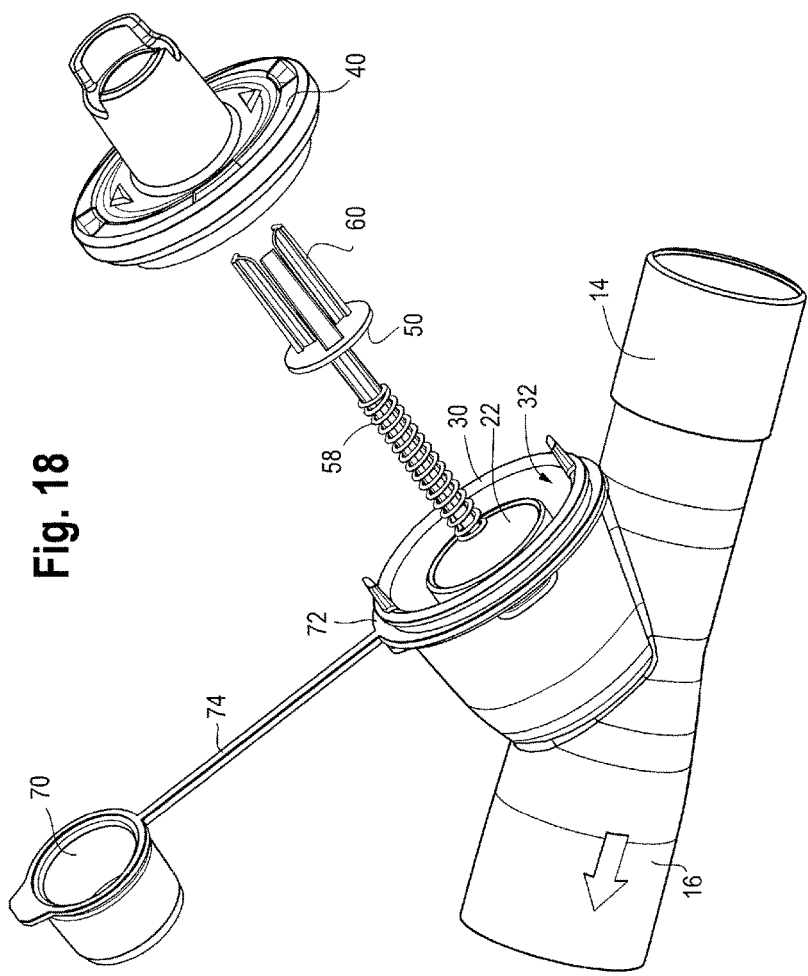
FIG. 18 shows an exploded view of one embodiment of an adapter.
Figure 20:
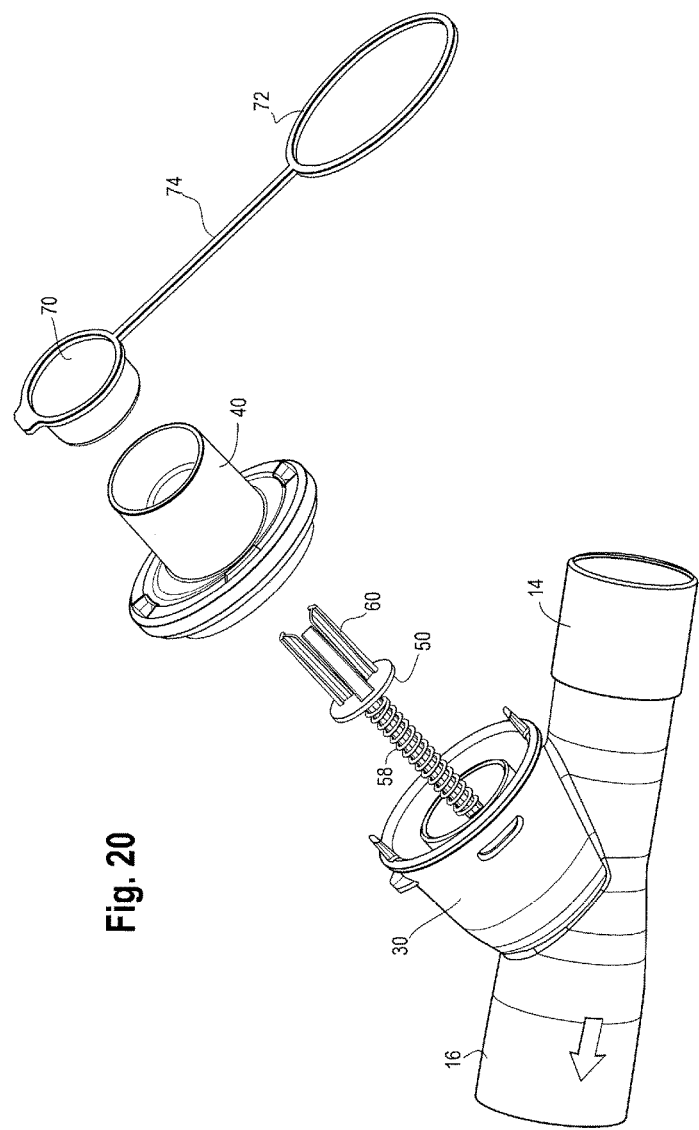
FIG. 20 shows an exploded perspective view of one embodiment of an adapter.
Figure 24:
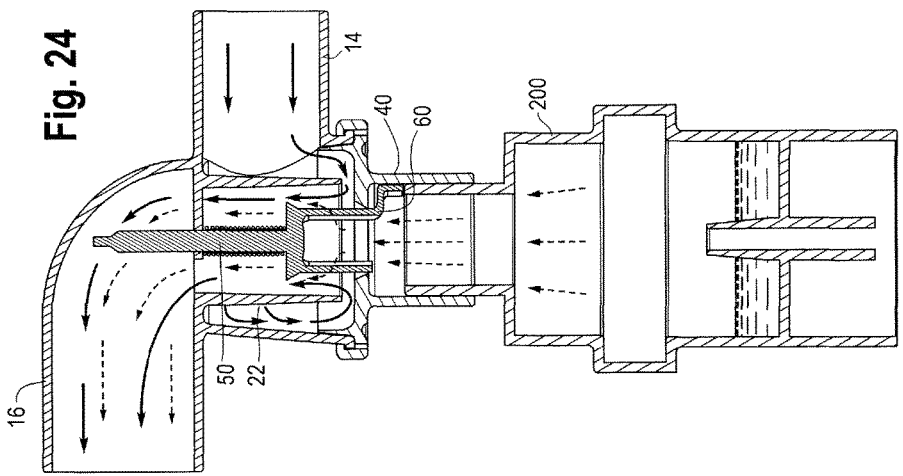
FIG. 24 shows a cross-sectional view of an alternative embodiment of an adapter.
Figure 50A:
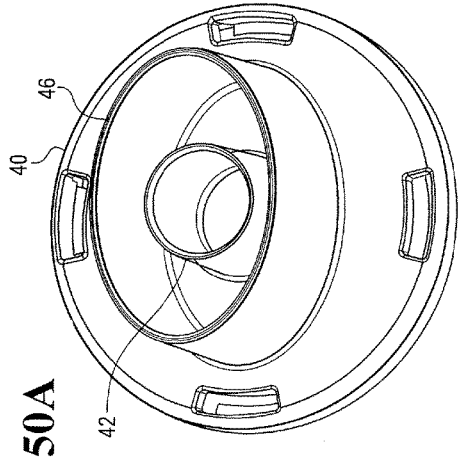
FIGS. 50A and B show top and bottom perspective views of one embodiment of a port.
Figure 50B:
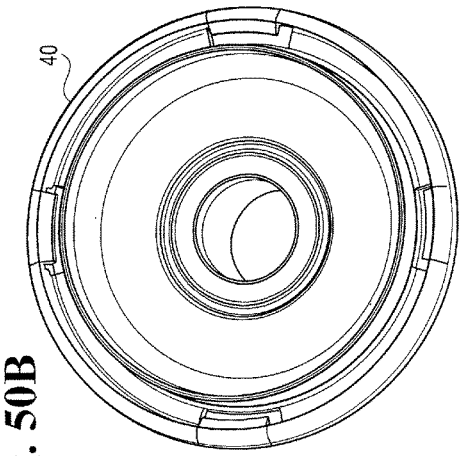
Figure 27:
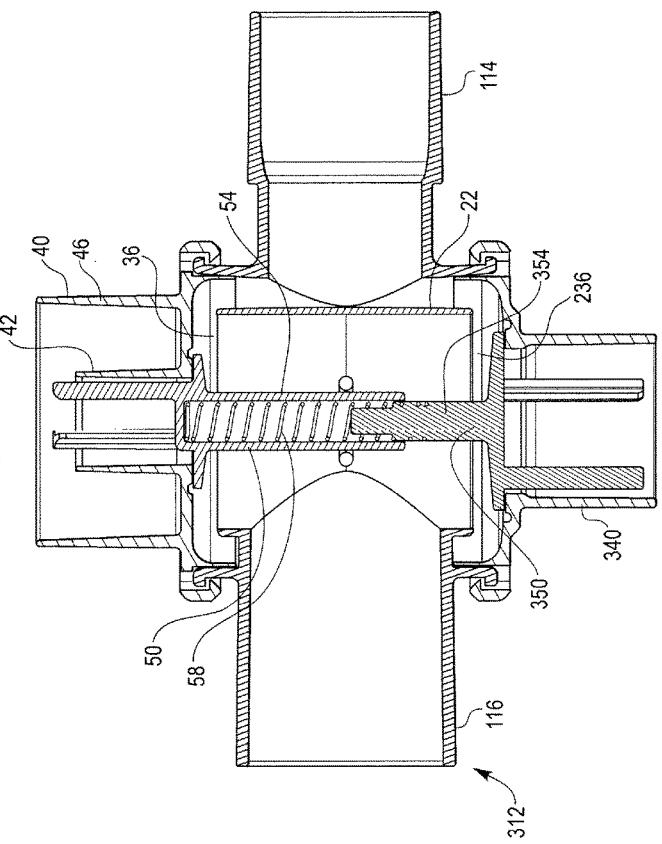
FIG. 27 shows a cross-sectional view of an alternative embodiment of an adapter.
Figure 28:
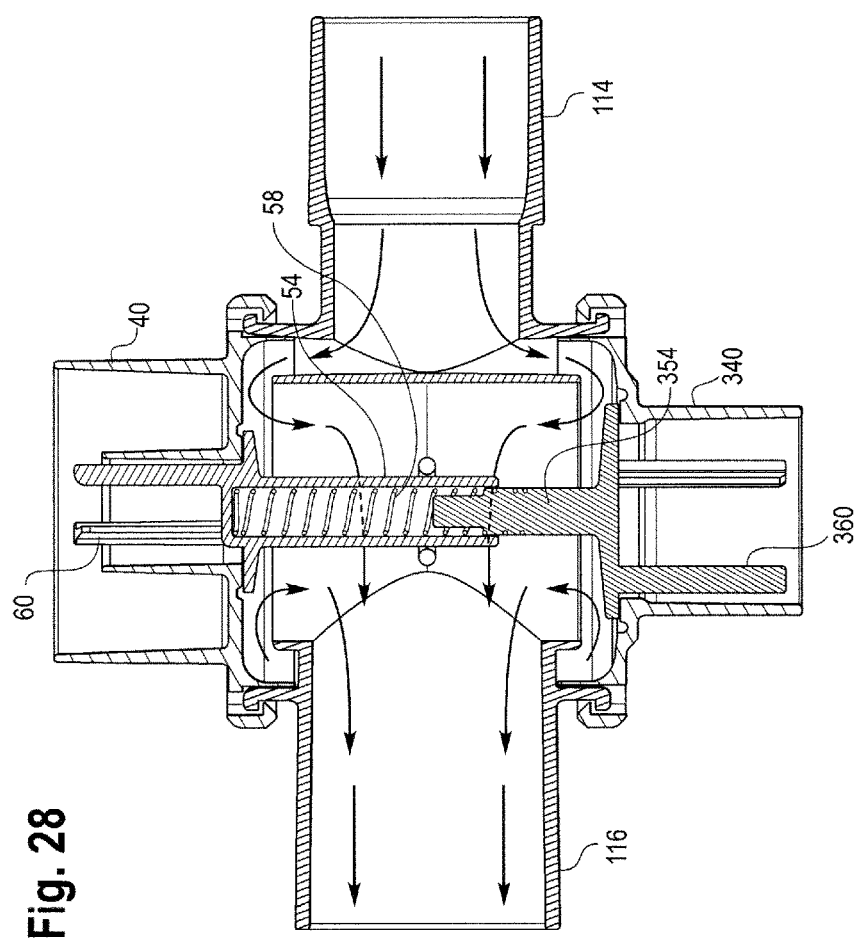
FIG. 28 shows a cross-sectional view of an alternative embodiment of an adapter.
Figure 30:
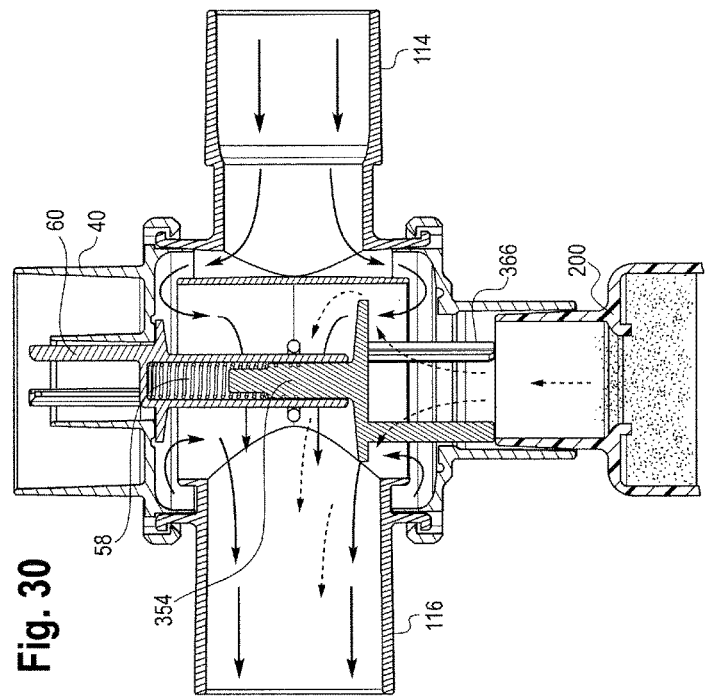
FIG. 30 shows a cross-sectional view of an alternative embodiment of an adapter.
Figure 29:
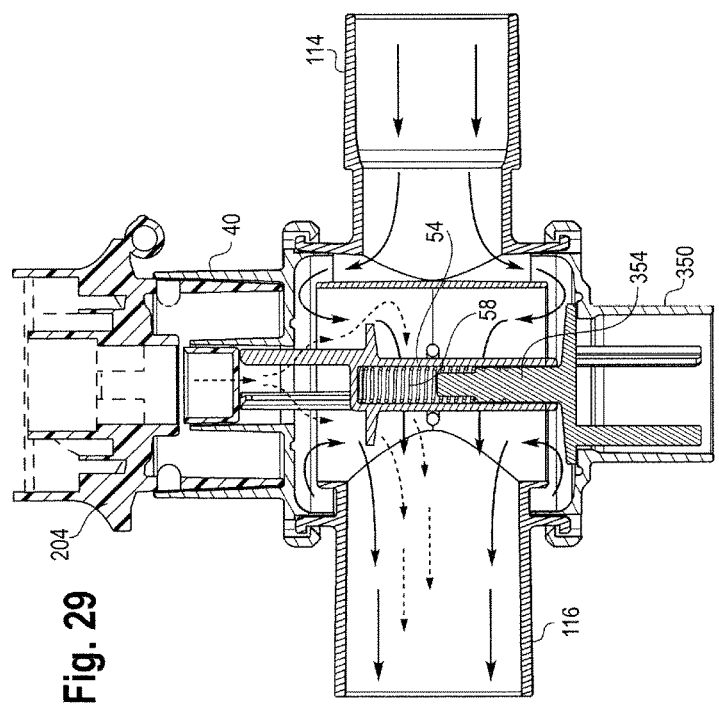
FIG. 29 shows a cross-sectional view of an alternative embodiment of an adapter.
Figure 33:
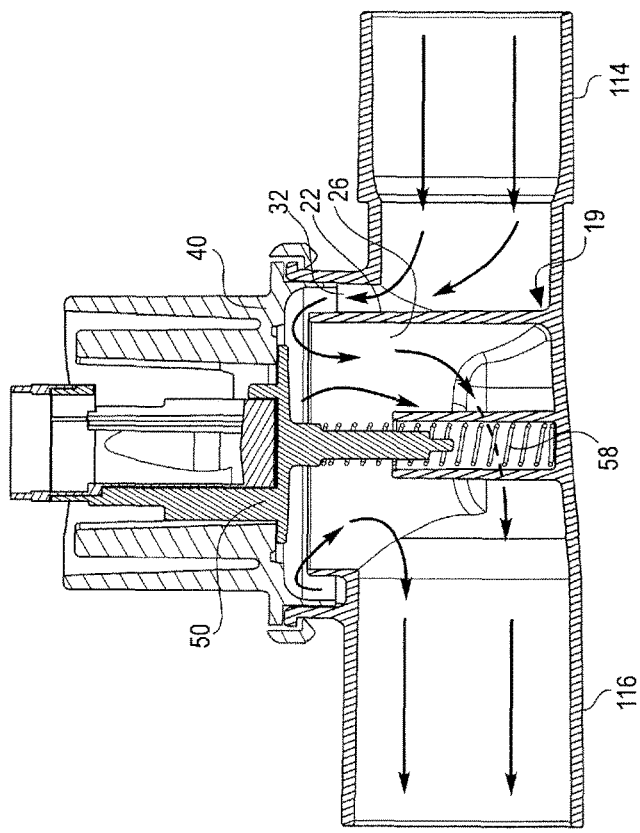
FIG. 33 shows a cross-sectional view of an alternative embodiment of an adapter.

Referring to FIGS. 18-20, a cap 70 may be tethered to the adapter with a retaining ring 72 and lanyard 74, and may be moved from an off position to an on position, wherein the cap covers the medicament delivery port 40 in the on position. The tethered cap 70 helps to maintain the ventilator circuit free from pressure leaks and dust particles. As shown in FIGS. 50A, B, the port may be configure with a non-cylindrical outer wall 46, for example an oval or elliptical shape, which surrounds the inner wall 42, which may be configure as a cylinder. In addition, one or more ribs or guards 307 may extend from the cap in a spaced apart relationship to the port as to protect the valve 50 and port 40.

Figure 23:
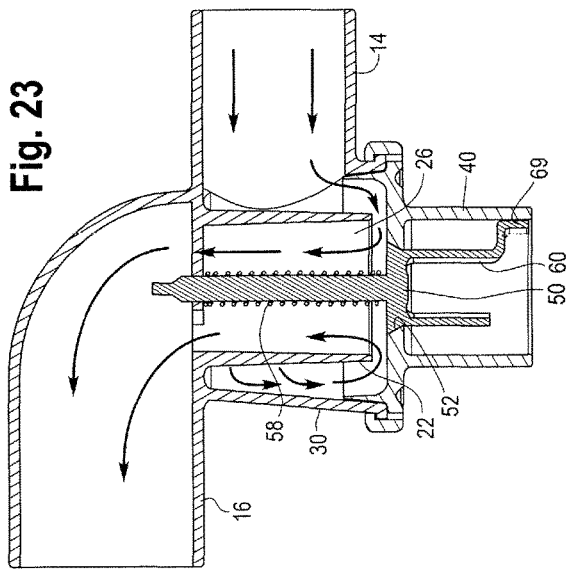
FIG. 23 shows a cross-sectional view of an alternative embodiment of an adapter.
Figure 25:
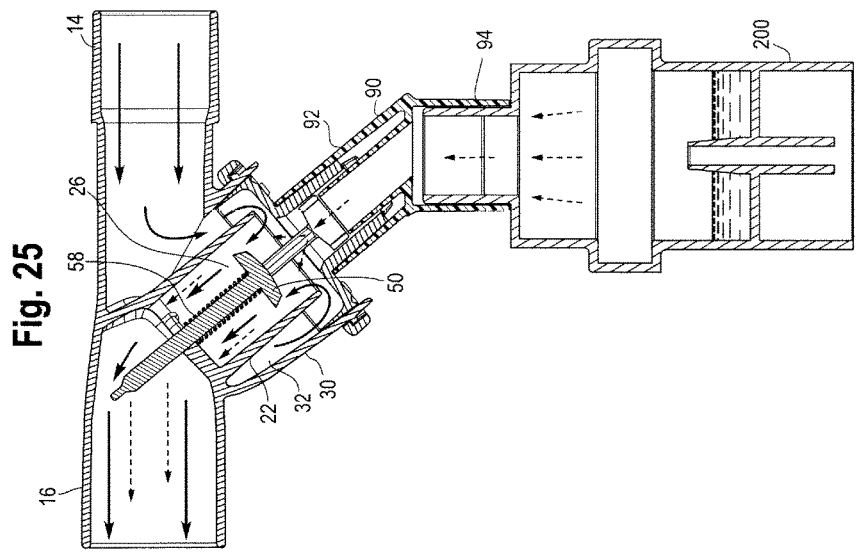
FIG. 25 shows a cross-sectional view of an alternative embodiment of an adapter.
Figure 26:
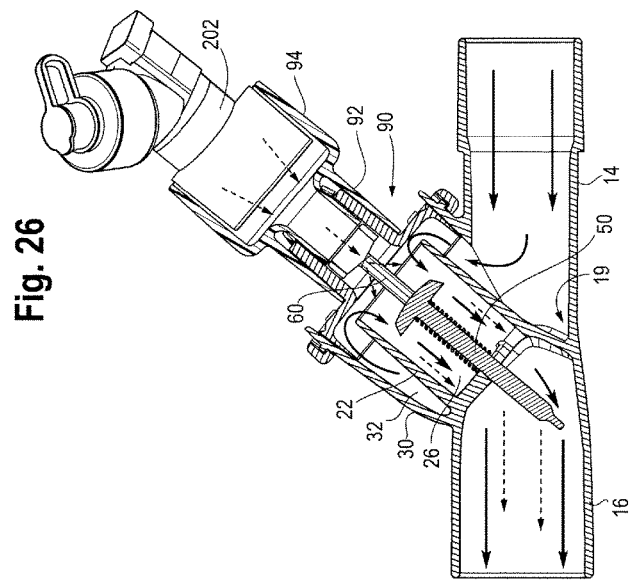
FIG. 26 shows a cross-sectional view of an alternative embodiment of an adapter.
Figure 32:
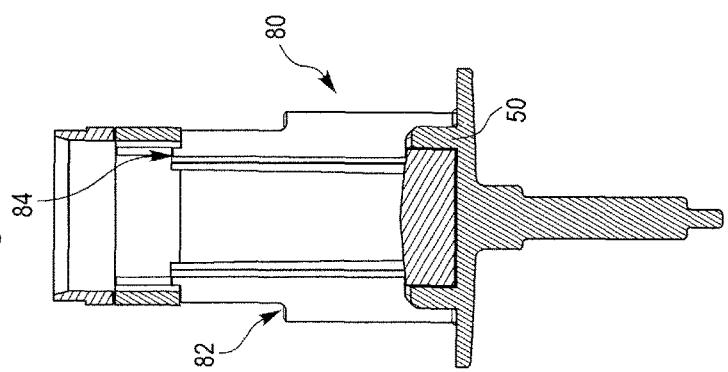
FIG. 32 shows a cross-sectional view of an alternative embodiment of an actuator.
Figure 34:
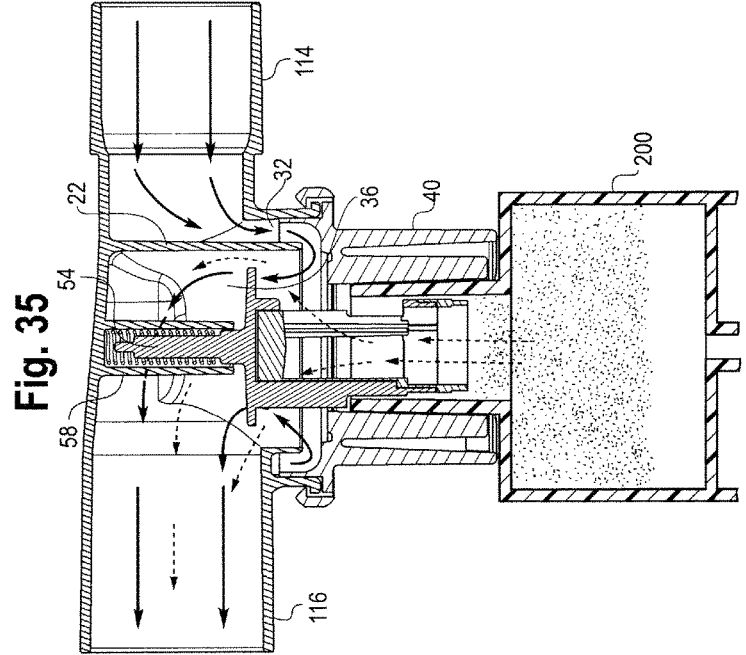
FIG. 34 shows a cross-sectional view of an alternative embodiment of an adapter.
Figure 35:
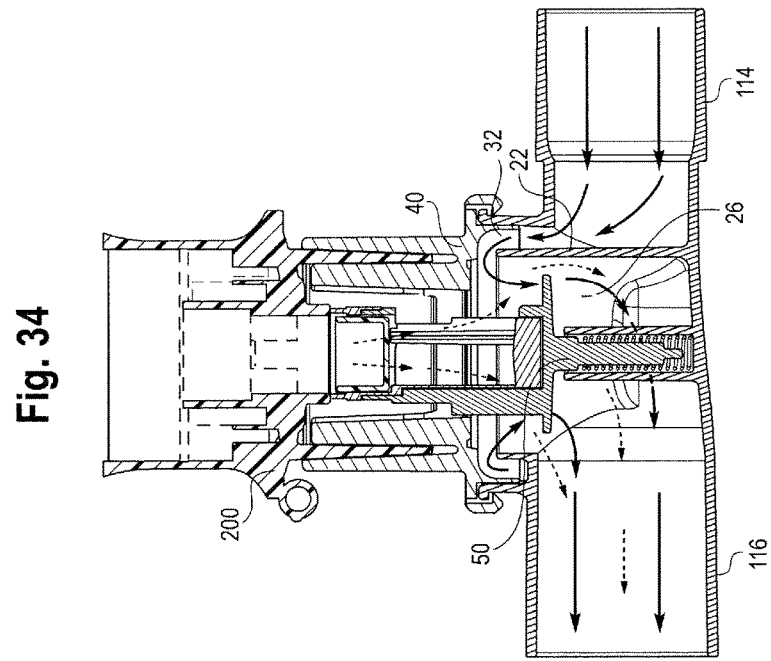
FIG. 35 shows a cross-sectional view of an alternative embodiment of an adapter.
Figure 36:
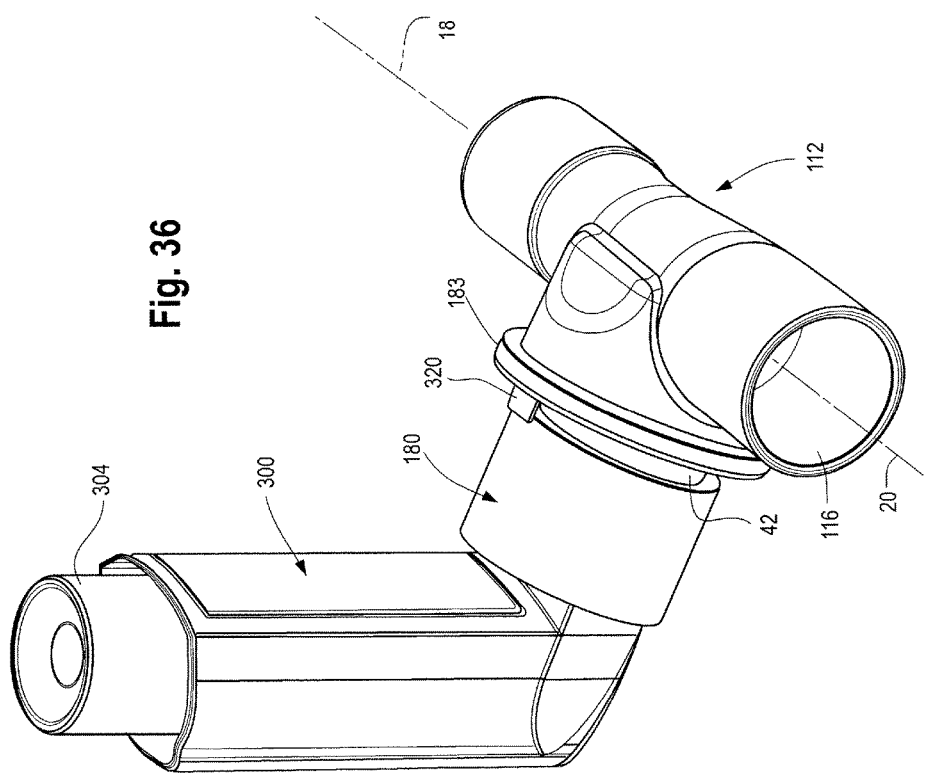
FIG. 36 shows an alternative embodiment of an adapter coupled to a pressurized metered dose inhaler.
Figure 37:
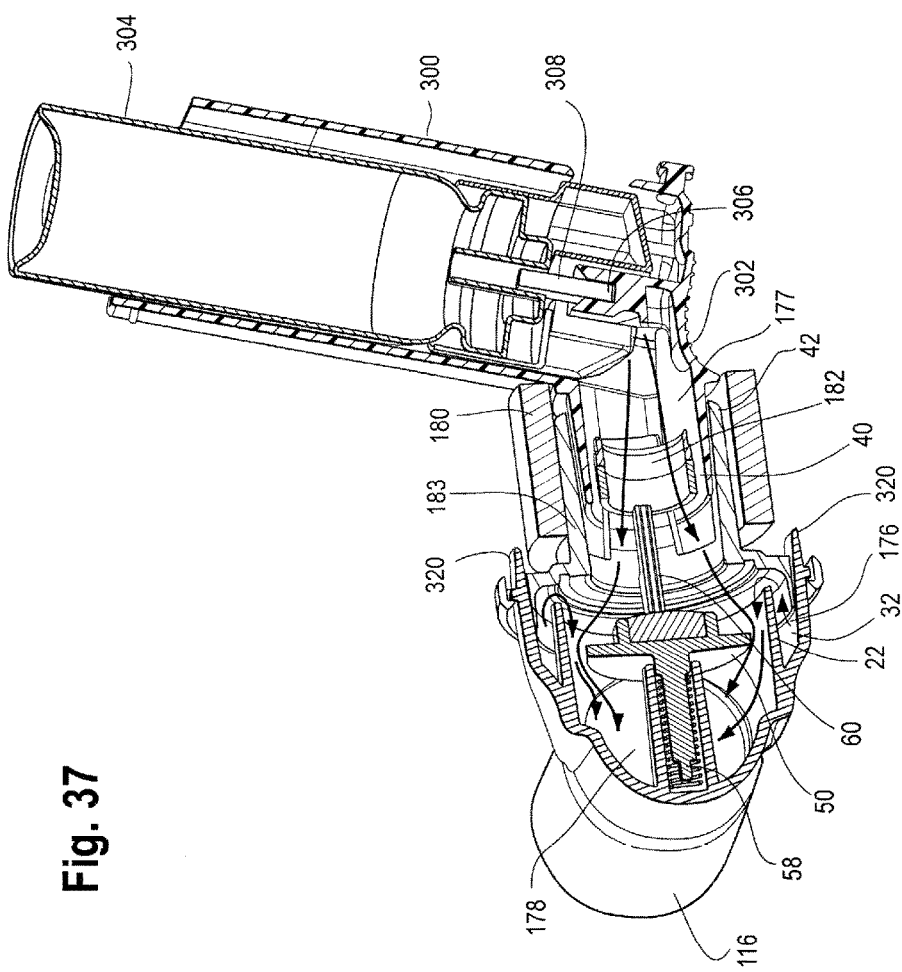
FIG. 37 shows a cross-sectional view of the embodiment shown in FIG. 36.
Figure 47:
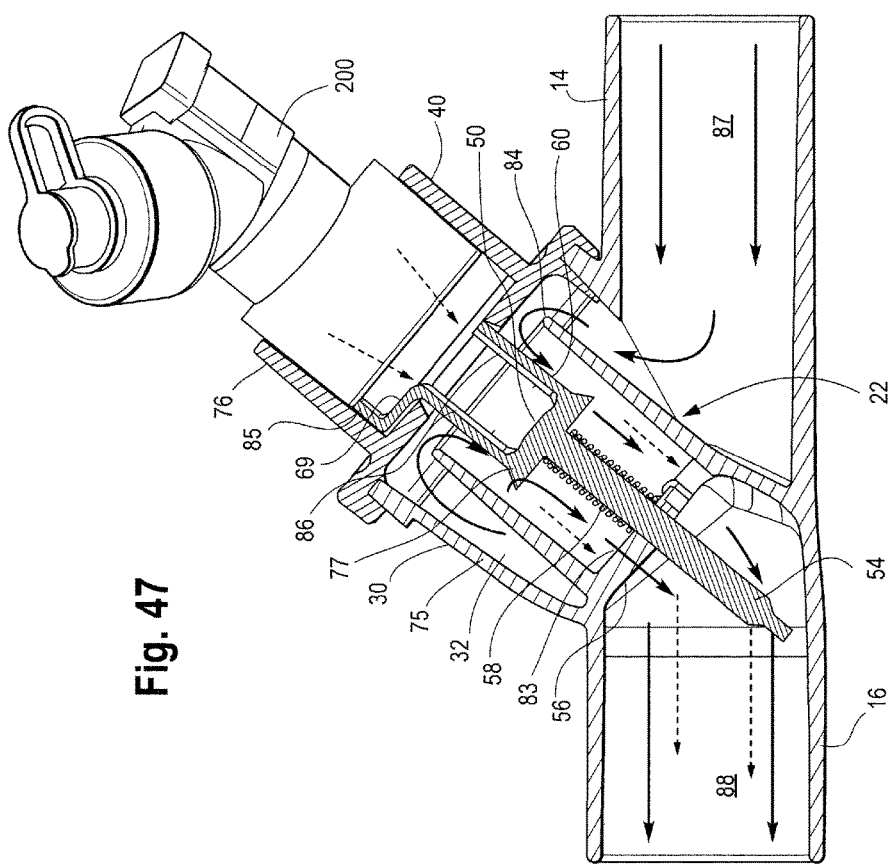
FIG. 47 shows a cross-sectional view of one embodiment of an adapter with an inhaler inserted therein.

The end 66, 68, 69 of the actuator 60 and/or port 40 may be configured to engage different types and shapes of medicament delivery devices 200, including various nebulizers, a Hudson RCI Micro Neb nebulizer, an Aerogen AeroNeb Solo nebulizer, a Respimat inhaler, and/or other delivery devices. For example, as shown in FIG. 32, an actuator 80 is provided with two engagement members 82, 84, shown as an end portion and a shoulder, which are dimensioned to be engaged by different types of delivery devices. Various delivery device and adapters 90 may be configured with first ends 92 that fit into the port 40 and actuate the valve, and second ends 94 that are shaped to receive the particular delivery device. Other delivery devices interact directly with the port, for example with an annular flange that is inserted into a channel 144 formed around the port or inside the port as shown. Referring to FIGS. 22, 23 and 47, the actuator includes an L-shaped end portion 69 that engages a delivery device.

Figure 40:
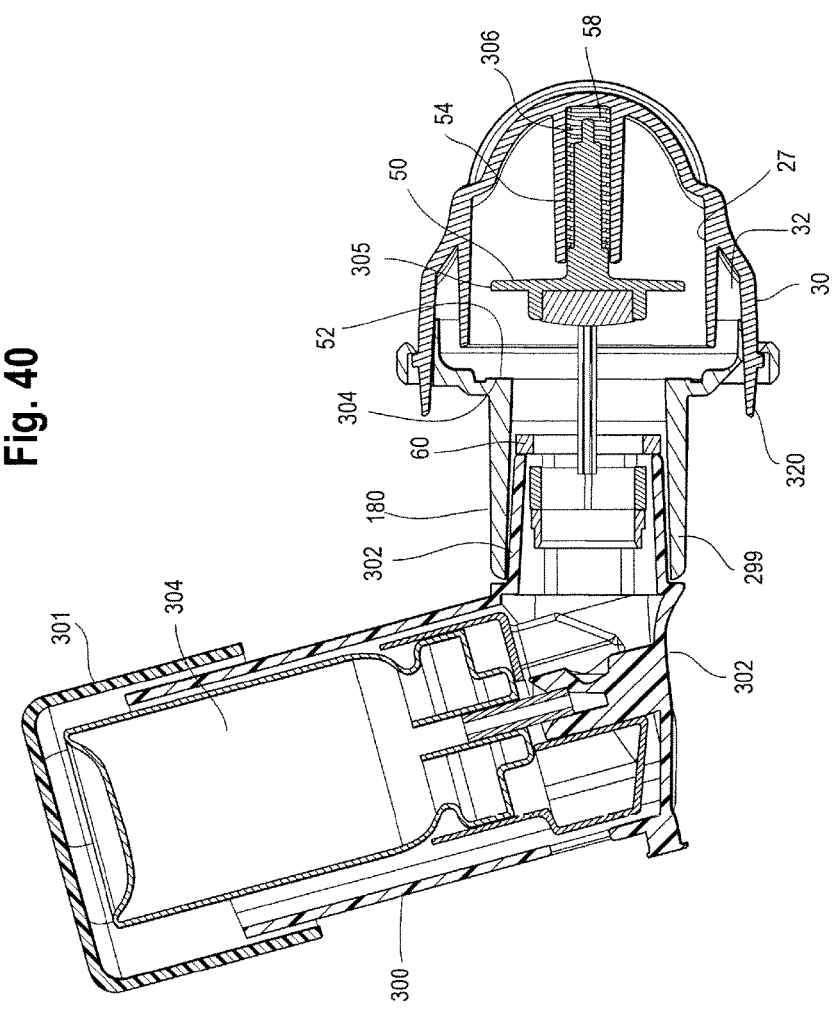
FIG. 40 shows a cross-sectional view of the embodiment taken alone line 40-40 of FIG. 39.
Figure 44:
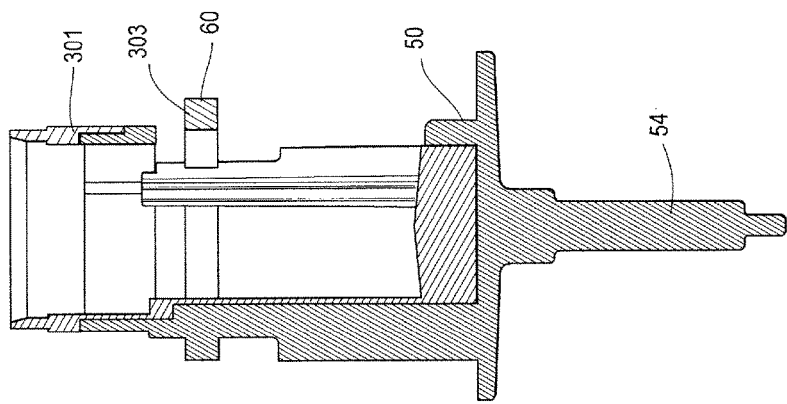
FIG. 44 shows a cross-sectional view of the valve taken along line 44-44 of FIG. 43.
Figure 43:
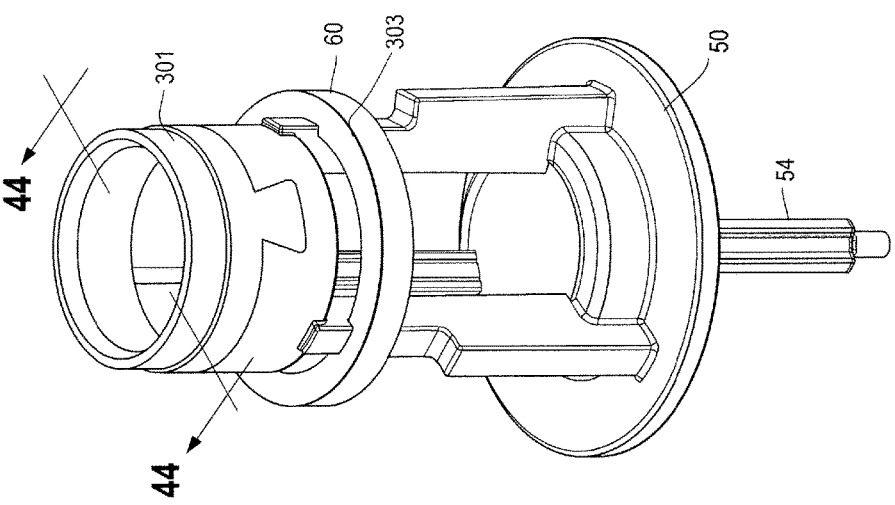
FIG. 43 shows a perspective view of a valve.
Figure 45:
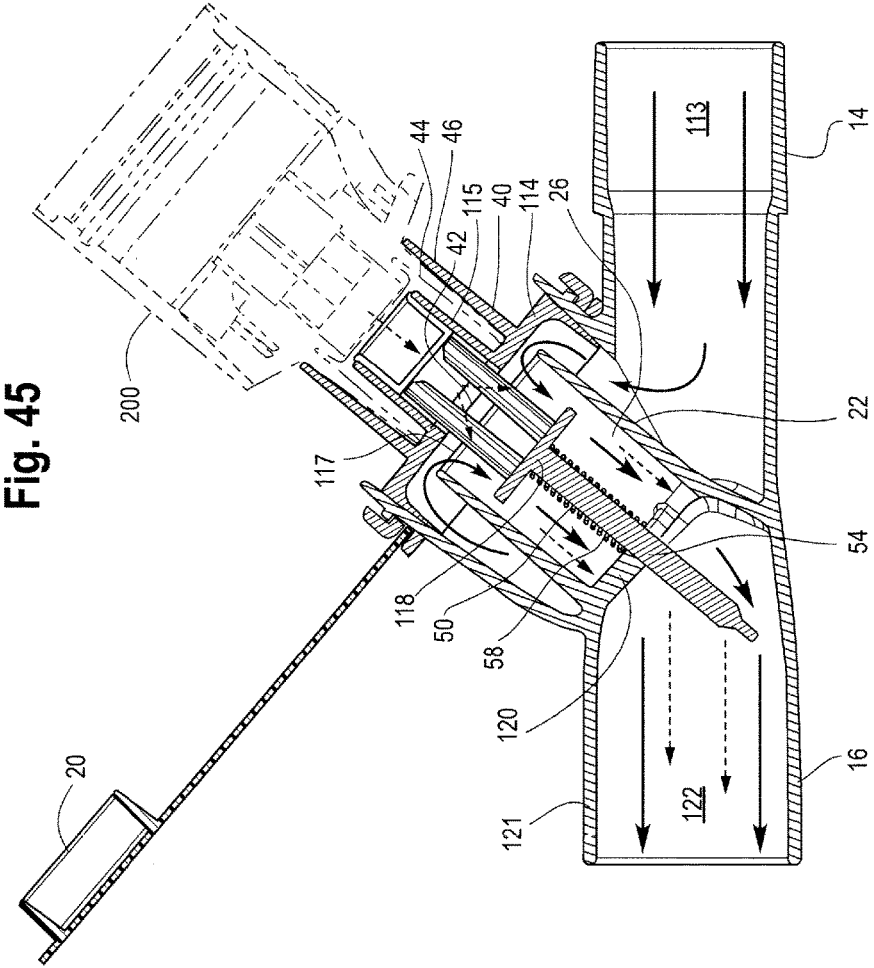
FIG. 45 shows a cross-sectional view of one embodiment of an adapter with an inhaler inserted therein.
Figure 46:
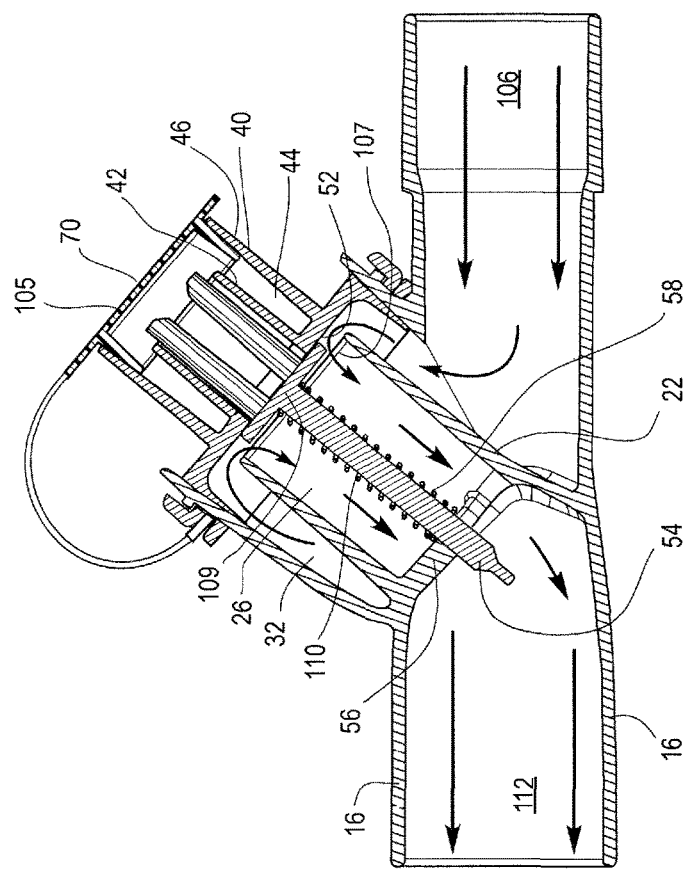
FIG. 46 shows a cross-sectional view of the adapter in FIG. 45 without an inhaler inserted therein.

For example, and referring to FIGS. 36-44, a pressurized metered dose inhaler (pMDI) is configured with a medicament container 304 that dispenses an aerosolized medicament, and an actuator boot configured with a housing 300 and an outlet 302, configured as a mouthpiece in one embodiment. A support block 306 extends interiorly of the housing and engages a valve stem 308 extending from the container. When the container 304 is depressed, a dose of medicament is dispensed through an orifice in the support block 306 and through the outlet 302. The mouthpiece 302 is engaged with an end 182 of the actuator 60, which moves the actuator 60 and valve 50 from a closed position to an open position against the force of the spring 58. As shown in FIGS. 43 and 44, the valve 50 includes a nose portion 303 that fits inside the mouthpiece and channels the medicament into the passageway 26. The actuator defines a ledge 303, against which the mouthpiece 302 engages. Once the valve 50 is open, the container may be actuated by moving it relative to the housing, thereby releasing a dose of medicament 177 through the mouthpiece 302, the nose portion 303 and into the interior passageway 26. The medicament 177 flow is mixed with the gas flowing from the exterior passageway 32 to the interior passageway 26, and thereafter to the outlet port 16. The housing 300 is coupled to a cap 183 of the adapter. For example, the mouthpiece 302 is inserted into the port 40, defined by the cap, and coupled thereto with a ring shaped connector or collar 180, made for example of rubber. The cap 183 is releasably coupled to the adapter housing with a pair of tabs 320 inserted through openings in the cap 183. As shown in FIGS. 38-40, a rubber cap 301 may be positioned over the end of the actuator boot to avoid leakage.

Referring to FIGS. 27-30, an adapter housing 312 has first and second mouths 36, 236 communicating between the exterior passageway 32 and the interior passageway 26 on opposite ends of the interior wall 22. First and second medicament delivery ports 40, 340 are positioned adjacent the first and second mouths. The ports may have different dimensions and shapes to accommodate different types of medicament delivery devices, for example with the port 46 having a channel shaped to receive the end of one type of device and the port 346 configured to receive the device therein. A second valve 350 is configured to move between a closed position wherein second valve closes the second medicament delivery port and an open position wherein the second medicament delivery port is open. As shown, the second valve 350 is in a closed position when the first valve 50 is in an open position, and the first valve is in a closed position when the second valve is in an open position. It should be understood, however, that both valves may be moved to the open position simultaneously. The first and second valves may have interfacing valve stems 54, 354, with one stem moveable within the other, and with a spring 58 acting between the valve stems to bias the valves to the closed position.

In operation, and referring to FIGS. 1-7, 10-31B and 33-37, the adapter 12, 112, 312 is inserted into a ventilator circuit 2. A gas flows along the flow path 18 through the inlet port 14, 114, circulates around the internal wall 22, 122 in the exterior passageway 32, 132 and passes over the edge 34, 134 and through the mouth 36, 136 to the interior passageway 26, 126, and then to the outlet port 16, 116, whereinafter the gas may be communicated to the patient through the user interface 6.

When a caregiver desires to deliver a medicament to the patient, a medicament delivery device 200, whether a nebulizer 202, inhaler 204 or other device, is inserted into the medicament delivery port 40, 140. The insertion causes the medicament delivery device, or an adapter connected thereto, to engage the actuator 60 and press it inwardly against the biasing force of the spring 58, thereby opening the valve 50 as it is moved off of the seat 52. The medicament may thereafter be administered by actuating the medicament delivery device 200, or the insertion and actuation of the device against the valve may administer the medicament. The medicament is dispensed into the flow of gas. Because of the circumferential flow, e.g., 360 degree flow, around the wall and through the mouth, the medicament is thoroughly and uniformly mixed with the gas. The flow eliminates any unnecessary turbulence in the flow, thereby increasing the performance of the device. The configuration of the wall 22, and its interface with the inlet port 18, helps to collect water created by humidity in the circuit, in a pooling area 19 at the bottom of the wall such that the water does not adversely affect the drug performance. After the treatment, the medicament delivery device 200 may be removed from the medicament delivery port 40, with the valve 50 thereafter closing the medicament delivery port opening.

The adapter thereby provides a high efficiency drug delivery method in a closed ventilation circuit, and is robust and simple including only an adapter and medicament delivery device. The system can be installed, and thereafter used, in a quick and easy fashion. The valve ensures a low microbiological risk. The valve prevents contaminants from entering the system at an earlier point of the inhaler insert passage way. The ventilator circuit is kept sealed from outside contamination at all times with or without the medicament delivery device in place, and the adapter can be a permanent feature of the ventilator circuit, thereby eliminating the need to temporarily break the circuit and disconnect the patient from the ventilator. By having a permanent connection, any losses in pressure are minimized. Also hospital personnel cross contamination is minimized. The spring loaded valve when closed is fully seated and out of the way of the air stream, minimizing any resistance to the flow, and or any leaks to the outside of the ventilator circuit.

The adapter may be made of polypropylene and/or MABS/Terlux, and the valve spring may be made of stainless steel, or plastic.

When a medicament delivery device is not seated in the port, the inspiratory air stream produced by the ventilator flows around and over the 360 degree cylindrical chamber, defined by the wall, under the fully seated actuator valve around the spring, and through the three spoke actuator guide to the outlet port.

When a medicament delivery device 200 is inserted into the port 46, friction with the wall of the port holds the device in place. The device pushes down the actuator and valve compressing the spring, and opening the passage where the drug flows out of the device. The inspiratory air stream produced by the ventilator flows around and over the 360 degree cylindrical chamber and carries the drug released by the inhaler. The air and drug mixture travel out of the cylindrical chamber through the three spoke actuator guide and to the outlet port of the adapter.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:
1. An adapter housing comprising:
an inlet port defining a flow path;
an outlet port in flow communication with said inlet port by way of a passageway;
a medicament delivery port opening into said passageway;
a valve moveable between a closed position wherein said valve closes said medicament delivery port and an open position wherein said medicament delivery port is open; and
an actuator coupled to and positioned upstream of said valve, wherein said actuator comprises an end portion defining a central channel, wherein said end portion is adapted to be received in a mouthpiece of a pressurized metered dose inhaler.

2. The adapter housing of claim 1 further comprising a collar removeably disposed around said medicament delivery port and adapted to secure a medicament delivery device to said medicament delivery port.

3. The adapter housing of claim 2 wherein said collar is made of rubber.

4. The adapter housing of claim 1 wherein said valve comprises a spring biasing said valve to said closed position.

5. The adapter housing of claim 1 wherein said actuator comprises at least one side opening formed therein and in flow communication with said central channel.

6. The adapter housing of claim 5 wherein said central channel is positioned upstream of said at least one side opening.

7. The adapter housing of claim 1 wherein said actuator comprises a ledge adapted to engage the mouthpiece of the pressurized metered dose inhaler.

8. A ventilator circuit comprising:
an oxygen supply;
a user interface; and
an adapter comprising:
an inlet port defining a flow path and in flow communication with said oxygen supply;
an outlet port in flow communication with said user interface, wherein said outlet port is in flow communication with said inlet port by way of a passageway;
a medicament delivery port opening into said passageway;
a valve moveable between a closed position wherein said valve closes said medicament delivery port and an open position wherein said medicament delivery port is open;
a medicament delivery device communicating with said medicament delivery port and comprising a mouthpiece; and
an actuator coupled to and positioned upstream of said valve, wherein said actuator comprises an end portion defining a central channel, wherein said end portion is disposed in said mouthpiece of said medicament delivery device.

9. The ventilator circuit of claim 8 further comprising a collar connecting the medicament delivery device with said medicament delivery port.

10. The ventilator circuit of claim 9 wherein said medicament delivery device comprises a pressurized metered dose inhaler comprising an actuator boot having said mouthpiece, wherein said collar is disposed around said medicament delivery port and said mouthpiece.

11. The ventilator circuit of claim 10 wherein said pressurized metered dose inhaler comprises a container of medicament disposed in said actuator boot, said actuator boot having an opening opposite said mouthpiece, and further comprising a cap member positioned over said opening of said actuator boot.

12. The ventilator circuit of claim 11 wherein said cap member is made of rubber.

13. The ventilator circuit of claim 9 wherein said collar is made of rubber.

14. The ventilator circuit of claim 8 wherein said valve comprises a spring biasing said valve to said closed position.

15. The ventilator circuit of claim 8 wherein said actuator comprises at least one side opening formed therein and in flow communication with said central channel.

16. The ventilator circuit of claim 15 wherein said central channel is positioned upstream of said at least one side opening.

17. The ventilator circuit of claim 8 wherein said actuator comprises a ledge engaged with an end of said mouthpiece.

18. A method of delivering a medicament comprising:
introducing a gas to an inlet port of an adapter along a flow path;
passing said gas through a passageway defined by said adapter;
opening a valve by inserting a mouthpiece of a pressurized metered dose inhaler into a medicament delivery port opening, engaging an actuator connected to said valve with said mouthpiece, and disposing an end portion of said actuator into an interior of said mouthpiece, wherein said end portion comprises a central channel;

actuating said pressurized metered dose inhaler and releasing a medicament through said central channel and into said medicament delivery port opening;

introducing said medicament from said medicament delivery port opening into said passageway and thereby entraining said medicament with said gas; and delivering said medicament to a user through an outlet port of said adapter communicating with said interior passageway.

19. The method of claim 18 further comprising removing said pressurized metered dose inhaler from said medicament delivery port opening and closing said medicament delivery port opening with said valve.

20. The method of claim 18 wherein said pressurized metered dose inhaler comprises an actuator boot having said mouthpiece.

21. The method of claim 20 wherein said pressurized metered dose inhaler comprises a container of medicament disposed in said actuator boot, said actuator boot having an opening opposite said mouthpiece, and further comprising covering said opening of said actuator boot with a cap member.

22. The method of claim 21 wherein said cap member is made of rubber.

23. The method of claim 18 wherein said actuator has at least one side opening formed therein and in flow communication with said central channel.

24. The method of claim 23 wherein said central channel is positioned upstream of said at least one side opening.

25. The method of claim 18 wherein said engaging said actuator connected to said valve with said mouthpiece comprises engaging a ledge defined on said actuator with an end of said mouthpiece of said pressurized metered dose inhaler.

26. The method of claim 18 further comprising coupling said pressurized metered dose inhaler to said medicament delivery port with a collar.

* * * * *